US011547700B2

(12) United States Patent
Chase et al.

(10) Patent No.: US 11,547,700 B2
(45) Date of Patent: *Jan. 10, 2023

(54) COMPOSITIONS AND METHODS FOR TREATING SYNUCLEINOPATHIES

(71) Applicant: CHASE THERAPEUTICS CORPORATION, Washington, DC (US)

(72) Inventors: Thomas N. Chase, Washington, DC (US); Kathleen E. Clarence-Smith, Washington, DC (US)

(73) Assignee: CHASE THERAPEUTICS CORPORATION, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,963

(22) Filed: Aug. 31, 2020

(65) Prior Publication Data

US 2020/0397761 A1    Dec. 24, 2020

Related U.S. Application Data

(63) Continuation of application No. 16/497,006, filed as application No. PCT/US2018/024344 on Mar. 26, 2018.

(60) Provisional application No. 62/528,228, filed on Jul. 3, 2017, provisional application No. 62/447,187, filed on Mar. 27, 2017.

(51) Int. Cl.
| | | |
|---|---|---|
| *A61K 31/428* | (2006.01) | |
| *A61K 31/4178* | (2006.01) | |
| *A61P 25/16* | (2006.01) | |
| *A61K 31/439* | (2006.01) | |

(52) U.S. Cl.
CPC ........ *A61K 31/428* (2013.01); *A61K 31/4178* (2013.01); *A61K 31/439* (2013.01); *A61P 25/16* (2018.01)

(58) Field of Classification Search
CPC ........................ A61K 31/428; A61K 31/4178
USPC ................................................ 514/367, 397
See application file for complete search history.

(56) References Cited

U.S. PATENT DOCUMENTS

| | | |
|---|---|---|
| 9,169,255 B2 | 10/2015 | Esposito et al. |
| 9,303,045 B2 | 4/2016 | Hitchcock et al. |
| 2005/0272722 A1 | 12/2005 | Lansbury et al. |
| 2008/0014259 A1 | 1/2008 | Bozik et al. |
| 2010/0105601 A2 | 4/2010 | Brady et al. |
| 2011/0071135 A1 | 3/2011 | Chase et al. |
| 2017/0015739 A1 | 1/2017 | Kallunki et al. |

FOREIGN PATENT DOCUMENTS

| | | |
|---|---|---|
| WO | 1996/018395 A1 | 6/1996 |
| WO | 2008/132712 A2 | 11/2008 |
| WO | 2009/109990 A2 | 9/2009 |
| WO | 2011/143721 A1 | 11/2011 |
| WO | 2014/039627 A1 | 3/2014 |
| WO | 2018/191408 A1 | 10/2018 |

OTHER PUBLICATIONS

"Pramipexole", CI0H17N3S, PubChem CID 119570, Jun. 24, 2006, pp. 1-80.
International Search Report for PCT/2019/064112 dated Feb. 10, 2020 (PCT/ISA/210).
Written Opinion for PCT/US2018/024344 dated Aug. 8, 2018 (PCT/ISA/237).
Huseyin Abali, M.D., et al., "Tropisetron, Ondansetron, and Granisetron for Control of Chemotherapy-Induced Emesis in Turkish Cancer Patients: A Comparison of Efficacy, Side-Effect Profile, and Cost", Cancer Investigation, Apr. 2007, pp. 135-139, vol. 25, col. 1, para 1.
Written Opinion for PCT/2019/064112 dated Feb. 10, 2020 (PCT/ISA/237).
International Search Report for PCT/US2018/024344 dated Aug. 8, 2018 (PCT/ISA/210).
Samuels et al. "Comparison of pramipexole with and without domperidone co-administration on alertness, autonomic, and endocrine functions in healthy volunteers" British Journal of Clinical Pharmacology. Jun. 19, 2007 (Jun. 19, 2007) vol. 64, p. 591-602; p. 591, abstract, para 2, p. 600, right col. para 2.
Jhee et al. "Centrally acting antiemetics mitigate nausea and vomiting in patients with Alzheimer's disease who receive rivastigmine" Clinical Neuropharmacology, vol. 25, No. 2, Mar. 1, 2002, pp. 122-123.
Makiguchi et al. "Mirtazapine-Induced Restless Legs Syndrome Treated With Pramipexole", The Journal of Neuropsychiatry and Clinical Neurosciences, Jan. 1, 2015, vol. 27; Issue 1, p. e76 https://neuro.psychiatryonline.org/doi/pdf/10.1176/appi.neuropsych.13120357.
Communication, dated Nov. 23, 2020, issued by European Patent Office in counterpart application No. 18 777 889.9.
Communication, dated Mar. 31, 2021, issued by the Eurasian Patent Office in counterpart application No. 2019 92284 (with translation).
Stimmel et al., "Mirtazapine: An Antidepressant with Noradrenergic and Specific Serotonergic Effects", Pharmacotherapy: The Journal of Human Pharmacology and Drug Therapy, vol. 17, Issue 1, pp. 10-21, Jan. 17, 2012 (3 pages total).
Boehringer Ingelheim International GmbH, "Highlights of Prescribing Information of Mirapex, Mirapex® (pramipexole dihydrochloride) tablets, for oral use", Initial U.S. Approval: 1997, Reference ID: 3965044, Revised: Jul. 2016 (28 pages total).

*Primary Examiner* — Charanjit Aulakh
(74) *Attorney, Agent, or Firm* — Sughrue Mion, PLLC

(57) ABSTRACT

The present invention describes the use of a 5HT3-antagonist, in combination with a 6-propylamino-4,5,6,7-tetrahydro-1,3-benzothiazole-2-amine, to reduce adverse effects and to facilitate the neuroprotective treatment of a patient suffering from a synucleinopathic disorder to enable a therapeutically effective 6-propylamino-4,5,6,7-tetrahydro-1,3-benzothiazole-2-amine daily dose without the dose-limiting adverse effects caused by pramipexole when administered alone.

11 Claims, No Drawings

COMPOSITIONS AND METHODS FOR TREATING SYNUCLEINOPATHIES

RELATED APPLICATIONS

This application is a continuation of U.S. application Ser. No. 16/497,006 filed Sep. 24, 2019 (allowed), which is a National Stage of International Application No. PCT/US2018/024344 filed Mar. 26, 2018, which claims the benefit of U.S. Provisional Patent Application Ser. No. 62/477,187, filed Mar. 27, 2017, and U.S. Provisional Patent Application Ser. No. 62/528,228, filed Jul. 3, 2017, the disclosures of which are incorporated herein in their entirety by reference.

FIELD OF THE INVENTION

The present invention pertains to the field of the treatment of synucleinopathies, i.e. of neurodegenerative disorders of the human central nervous system, and in particular of the treatment of neurotoxic processes due to alpha-synuclein oligomerization and aggregation.

OBJECT OF THE INVENTION

The present invention concerns new combinations, compositions, and methods for treating synucleinopathies, including pharmaceutical combinations comprising an antagonist of the serotonin receptor subtype-3 ("5HT3-antagonist") and 6-propylamino-4,5,6,7-tetrahydro-1,3-benzothiazole-2-amine.

Definitions

"CNS": Central Nervous System.
"IR": Immediate Release of the active ingredient from a composition.
"ER": Extended Release of the active ingredient from a composition.
"GI": Gastro-Intestinal.
"AE(s)": Adverse Effect(s).
"SNCA": Synuclein-alpha or alpha-synuclein.
"MSA": Multiple System Atrophy.
"PD": Parkinson's Disease.
"LBD": Lewy Body Dementia.
"AD": Alzheimer's Disease.
"Synucleinopathy": A disease characterized by the abnormal accumulation, processing, and spreading of alpha-synuclein (α-synuclein) in the brain. Namely, α-synuclein deposits in the central, peripheral, and autonomic nervous system. Synucleinopathies (also called α-synucleinopathies) are neurodegenerative diseases which include, but are not limited to Parkinsons' disease, Lewy body dementia (LBD) or dementia with Lewy bodies (DLB), Alzheimer's disease, the Lewy body variant of AD, multiple system atrophy, neurodegeneration with brain iron accumulation, and parkinsonian disorders associated with glucocerebrosidase (GBA) mutations.
"TTS": Transdermal Therapeutic System.
"Effective daily dose of 5HT3-antagonist": this expression, as used herein, refers to a dose of said 5HT3-antagonist that is at least as high as that to prevent or treat nausea and vomiting in pediatric or adult patients undergoing cancer chemotherapy according to the current protocols for said treatment. Said daily dose normally is from 1 µg to 300 mg.
"6-Propylamino-4,5,6,7-tetrahydro-1,3-benzothiazole-2-amine": a chiral chemical compound that is available as racemate, chemically (R,S)-6-propylamino-4,5,6,7-tetrahydro-1,3-benzothiazole-2-amine, as (R)-stereoisomer, chemically (R)-6-propylamino-4,5,6,7-tetrahydro-1,3-benzothiazole-2-amine ("dexpramipexole", INN), and as (S)-stereoisomer, chemically (S)-6-propylamino-4,5,6,7-tetrahydro-1,3-benzothiazole-2-amine ("pramipexole", INN). These three chemical entities are basic substances that may be isolated each as an acid addition salt and solvate thereof. Pramipexole dihydrochloride monohydrate is also known with its USAN "pramipexole hydrochloride". As used herein, "6-propylamino-4,5,6,7-tetrahydro-1,3-benzothiazole-2-amine" is a general term that, unless otherwise specified, designates a member selected from the group consisting of pramipexole, the racemate, and a pramipexole/dexpramipexole mixture.
"(R)/(S)-mixture": this term designates a dexpramipexole/pramipexole physical mixture used as an active ingredient according to the present invention.
"(S)-enantiomer": this term, as used herein with reference to 6-propylamino-4,5,6,7-tetrahydro-1,3-benzothiazole-2-amine doses (daily or per unit form) designates the (S)-stereoisomer, included in said doses that, in said 6-propylamino-4,5,6,7-tetrahydro-1,3-benzothiazole-2-amine, are primarily responsible for the dopaminergic action counteracted by the 5HT3-antagonist. More specifically, S-enantiomer is herein used to designate the S-stereoisomer that is present in the racemate or pharmaceutically acceptable salt thereof, and similarly, to designate the pramipexole or pharmaceutically acceptable salt thereof that is present, as (S)-constituent, in a (R)/(S)-mixture, in order to distinguish it from pramipexole used alone.

The terms "6-propylamino-4,5,6,7-tetrahydro-1,3-benzothiazole-2-amine", (R)-6-propylamino-4,5,6,7-tetrahydro-1,3-benzothiazole-2-amine", "dexpramipexole", "pramipexole", "(S)-6-propylamino-4,5,6,7-tetrahydro-1,3-benzothiazole-2-amine", "(S)-enantiomer", "racemate" and "(R)/(S)-mixture" include the free bases and pharmaceutically acceptable salts thereof (unless otherwise specified); and the relative doses (daily or per unit form) are given in equivalents of pramipexole dihydrochloride monohydrate.

"Effective pramipexole dose/unit form", or "effective (S)-enantiomer dose/unit form": a dose per unit form of pramipexole or pharmaceutically acceptable salt thereof, or of (S)-enantiomer or pharmaceutically acceptable salt thereof, that is equivalent to from 0.125 mg to 42 mg of pramipexole dihydrochloride monohydrate. As noted above and as used herein, "pramipexole" and "(S)-enantiomer" refer to the same chemical entity, but the term "(S)-enantiomer" is generally used when describing the composition of the racemate and mixtures.

BACKGROUND OF THE INVENTION

Alpha-synuclein, a protein composed of 140 amino acids encoded by the SNCA (Synuclein-Alpha) gene, is abundantly expressed in the human brain and is mainly found in neuronal terminals, especially in the cortex, hippocampus, substantia nigra and cerebellum, where it contributes to the regulation of neurotransmitter release, and passes into the blood (Marques and Outeiro, 2012), packaged in exosomes originating from the CNS (Shi et al, 2014).

Under normal circumstances, this soluble protein appears to form a stably folded tetramer that resists aggregation. But, in certain pathological conditions, for unknown reasons, the alpha-synuclein oligomerizes and aggregates (with the formation of fibrils). Somewhere along this aberrant pathway, toxic synuclein species are believed to be formed which also pass into the peripheral circulation, carried within exosomes.

Aberrant alpha-synuclein oligomerization and aggregation are thought to be the cause of synucleinopathies, notably PD, LBD, parkinsonian disorders associated with glucocerebrosidase (GBA) mutations, MSA, multiple system atrophy, some forms of Alzheimer's disease, and several other disorders, which are collectively referred to as "synucleinopathies". Alpha-synuclein is a ubiquitous protein that is especially abundant in the brain and has been postulated to play a central role in the pathogenesis of Parkinson's disease (PD), Alzheimer's disease, and other neurodegenerative disorders (Kim et al. 2004).

An abnormal ratio of monomeric to oligomeric synuclein species in plasma exosomes of a patient is proposed to be a diagnostic hallmark of a synucleinopathy.

PD is a common neurodegenerative disorder of the human CNS, first described by James Parkinson in 1817. It has three major clinical signs: resting tremor, bradykinesia, and muscular rigidity. In addition, postural instability and various neurobehavioral disabilities may occur. In the US alone it is estimated that over 1 million individuals are afflicted by this inexorably progressive disorder. Moreover, PD prevalence continues to rise along with the general aging of the American population. Parkinsonian signs are now believed to largely reflect a progressive loss of dopaminergic neurons within the nigrostriatal system. The cause of this degenerative process remains incompletely understood, but now appears to involve the misprocessing of alpha-synuclein into abnormal neurotoxic species.

LBD is one of the most common types of progressive dementia. The central features of LBD include progressive cognitive decline, visual hallucinations, and parkinsonian motor symptoms, such as slowness of movement, difficulty walking, and muscular rigidity. Some may also suffer from depression. The symptoms of LBD are caused by the selective loss of nerve cells, presumably a result of synuclein misprocessing and associated with the build-up of Lewy bodies—spherical synuclein accumulations inside many of the degenerating neurons. Researchers do not know why alpha-synuclein accumulates into Lewy bodies or how synuclein species can cause the symptoms of LBD. The formation of LBDs have been considered to be a marker for PD; however, LBDs have also been observed in up to 60% of both sporadic and familial cases of Alzheimer's disease (AD) (Al-Mansoor et al. 2013). Accordingly, the aggregation of α-synuclein has been strongly implicated as a critical step in the development of neurodegenerative diseases (Al-Mansoor et al. 2013).

PD or brainstem-predominant type LBD and LBD or dementia with Lewy bodies (DLB) are the two most frequent α-synucleinopathies, and are progressive multisystem neurodegenerative disorders with widespread occurrence of α-synuclein deposits in the central, peripheral, and autonomic nervous system (Jellinger K A 2008). Reportedly, there is considerable clinical and pathologic overlap between PD (with or without dementia) and DLB (or LBD), corresponding to Braak LB stages 5 and 6, both frequently associated with variable Alzheimer-type pathology (Jellinger K A 2008). Dementia often does not correlate with progressed stages of LB pathology, but may also be related to concomitant Alzheimer lesions or mixed pathologies (Jellinger K A, 2008a).

Alzheimer disease (AD) has been reported to be featured by deposition of β-amyloid peptides, phosphorylated tau protein (3- and 4-repeat tau) and α-synuclein (aSyn) deposits (Jellinger K A, 2008b). Lewy body diseases (LBD), such as sporadic Parkinson disease (PD) and dementia with Lewy bodies (DLB), show aSyn-positive deposits in neurons, neurites, glia, and presynaptic terminals, while frontotemporal dementias present tau-positive and tau-negative, ubiquitin- and TDP-43-positive neuronal and glial inclusions (Jellinger K A, 2008b). Molecular interactions between major proteins, which may occur within the same brain in various distribution patterns, are associated with various phenotypes and mixed pathologies, e.g. AD with aSyn pathology in the brainstem and amygdala, PD and DLB with AD lesions, and frontotemporal dementia with a mixture of various deposits, while others are featured by one principal pathology without other lesions (e.g. tangle-predominant type of dementia, pure PD, brainstem-predominant LBD) (Jellinger K A, 2008b).

MSA with orthostatic hypotension is the current term for a neurological disorder that was once called Shy-Drager syndrome. A progressive disorder of the central and autonomic nervous systems, it is characterized by orthostatic hypotension (an excessive drop in blood pressure when standing up), which causes dizziness or fainting. Multiple system atrophy can occur without orthostatic hypotension, but instead have urinary tract involvement (urgency/incontinence). Neurologists classify the disorder into 3 types: the Parkinsonian-type includes symptoms of Parkinson's disease such as slow movement, stiff muscles, and tremor; the cerebellar-type, which causes problems with coordination and speech; and the combined-type, which includes symptoms of both parkinsonism and cerebellar failure. Problems with urinary incontinence, constipation, and sexual impotence in men happen early in the course of the disease. Other symptoms include generalized weakness, double vision or other vision disturbances, difficulty breathing and swallowing, sleep disturbances, and decreased sweating. Because the disease resembles others, a correct diagnosis may take years.

Mutations in the glucocerebrosidase gene (GBA) can result in the autosomal recessive disorder Gaucher disease. Different lines of evidence suggest that mutant GBA may be a risk factor for Parkinson's disease. GBA mutations are now thought to be the single largest risk factor for development of idiopathic PD. Clinically, on imaging and pharmacologically, GBA PD is almost identical to idiopathic PD (O'Regan et al, 2017). The molecular mechanisms which lead to this increased PD risk in GBA mutation carriers are not fully elucidated, but have been shown to be associated with accumulation of synuclein (Soria et al, 2017).

Several other disorders have also, albeit less frequently, been considered to be synucleinopathies. These include Hallevorden-Spatz syndrome, neuronal axonal dystrophy and some cases of traumatic brain injury. In the case of Hallevorden-Spatz syndrome, symptoms include parkinsonism, dystonia, dysphagia/dysarthria, rigidity/stiffness of limbs, dementia, and spasticity.

Many now believe that processes leading to synuclein aggregation may be central to the neuronal injury and destruction occurring in these synucleinopathic disorders.

The mechanism of aggregation in these synucleinopathies remains uncertain. Current evidence suggests that the conversion of an alpha helical structure into a beta pleated conformation and subsequent oligomerization might be the pathogenic antecedents to the fibrillization and aggregation of synuclein. These characteristics are similar to the aberrant processing of prion protein that also can become highly neurotoxic. Phosphorylation of alpha-synuclein at the serine-129 residue has been implicated as a contributory factor (Chen et al. 2016). According to this author, a prion form of alpha-synuclein could be a causal agent, especially for multiple system atrophy. Prions are small proteins that also can misfold, oligomerize, aggregate and propagate to other cells. The result in brain is a profound and spreading neurotoxic process.

Accordingly, inhibiting the initial misfolding, oligomerization and aggregation of synuclein may be beneficial in slowing or even arresting the progression of synucleinopathic disorders.

As mentioned above, alpha-synuclein is readily excreted into extracellular spaces and has been identified in cerebrospinal fluid, blood, urine, and saliva (Marques and Outeiro, 2012). The mechanisms of alpha-synuclein excretion are not fully understood, but studies have demonstrated that at least a fraction of alpha-synuclein is excreted within exosomes, the 40 to 100 nm membrane vesicles of endocytic origin (reviewed in Shi et al. 2014). The ratio of monomeric to oligomeric species in plasma exosomes originating from the CNS may correlate with disease severity (Shi et al. 2014), thus suggesting that plasma exosomal alpha-synuclein species can help monitor disease progression.

Similarly, exosomal alpha-synuclein levels correlated with severity of impairment in cross-sectional samples from patients with LBD (Stuendl et al. 2016).

Based on the above, drugs that normalize the ratio of monomeric to oligomeric alpha-synuclein species in plasma exosomes deriving from brain should slow or even arrest the neurodegenerative process associated with synucleinopathies.

Various compositions for the treatment of PD-associated synucleinopathy and related disorders that target initial synuclein oligomerization and aggregation have been proposed. The discovery process primarily involves cellular and animal models of prion- and synuclein-induced neurodegeneration (Prusiner et al. 2015). Unfortunately, none of these models has been validated and all are currently regarded uncertain predictors of effects in humans. Nevertheless, these models continue to be widely used in the absence of better discovery techniques.

Pharmaceutical agents currently proposed for consideration include, for instance, such small molecules as pramipexole and its analogues.

Pramipexole is a synthetic aminothiazole derivative described in U.S. Pat. No. 4,886,812, the contents of which are incorporated herein by reference in their entirety. It is a dopamine agonist of the non-ergoline class (Schneider C S and Mierau J, 1987) that is approved for the treatment of the motor symptoms of Parkinson's disease (PD), in doses ranging from 0.375 mg/day to 4.5 mg/day, given in 3 equally divided doses (Mirapex® Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 4.5 mg of pramipexole dihydrochloride monohydrate.

Although pramipexole is widely used for the relief of parkinsonian symptoms, its potential as a disease modifying agent has made it the object of considerable investigative attention.

Pramipexole reportedly diminishes synuclein oligomer formation in vitro (Ono et al. 2013). Related studies suggest that pramipexole inhibits the toxic effects of rotenone on dopaminergic neurons in a mouse PD model while reducing immunoreactivity for alpha-synuclein; additionally, pramipexole decreases the in vitro oligomerization of human wild-type alpha-synuclein by $H_2O_2$ plus cytochrome c (Inden et al. 2009). Pramipexole has also been observed to inhibit the aggregation of alpha-synuclein in human neuroblastoma SH-SY5Y cells (Kakimura et al. 2009). Importantly, the relative expression of α-synuclein in serum exosomes has been found to decline during pramipexole treatment of PD-type patients (Luo et al. 2016).

In addition, it began to be reported that pramipexole can exert neuroprotective effects in various in vitro cellular and in vivo animal models of PD. Mechanisms by which these protective effects may occur remain uncertain. Unfortunately, the protective effects of pramipexole in animal models are generally small and require higher doses than considered safe and tolerable for human administration. It is thus hardly surprising that pramipexole, in doses approved for the treatment of motor symptoms of PD failed to evidence neuroprotective (i.e., disease modifying) activity in a randomized, controlled, clinical trial involving 535 PD patients (Schapira A H 2013).

(R)/(S)-mixtures, consisting of pharmaceutical compositions comprising a therapeutically effective amount of dexpramipexole or pharmaceutically acceptable salts and solvates thereof and a therapeutically effective amount of pramipexole or pharmaceutically acceptable salts and solvates thereof, useful for the treatment of PD, are disclosed in US 2008/0014259, the content of which are incorporated herein by reference in its entirety.

According to US 2008/0014259, both enantiomers are able to confer neuroprotective effects by their ability to accumulate in brain cells, the spinal cord and mitochondria where they exert a positive effect on neurological function that is independent of the dopamine agonist activity of pramipexole. In particular, said document proposes said composition as a neuroprotective agent and a therapeutically effective amount of from about 0.0625 mg to about 6 mg of pramipexole in combination with up to 5000 mg of dexpramipexole. However, this document emphasizes the pramipexole adverse effects due to its dopaminergic action and tends to privilege pramipexole low doses, as also confirmed by the same applicant in the almost concurrent WO 2008/113003, the contents of which are incorporated herein by reference in their entirety.

According to US 2013/0116292, the contents of which are incorporated herein in their entirety by reference, dexpramipexole, or pharmaceutically acceptable salts and solvates thereof, acts by slowing the progression of neuronal degeneration and/or by preventing neuronal cell death. However, no further mention of this possible noteworthy action of dexpramipexole appeared in the literature.

A synthesis of dexpramipexole and of pharmaceutically acceptable salts thereof, in particular dexpramipexole dihydrochloride monohydrate, is described in US 2012/0253047, the contents of which are incorporated herein by reference in their entirety.

Unfortunately, limitations associated with the administration of pramipexole to synucleinopathic patients limit its use at the potentially higher neuroprotective doses predicted by many animal models. First, mechanisms to explain its putatively beneficial effects on synuclein-related neurotoxicity continue to elude full understanding. Second, effect sizes in animal model studies tend to be small and occur only at relatively high drug doses. Both situations were also observed in the above mentioned report of pramipexole-induced changes in exosomal synuclein in PD patients, which were associated with the administration of the highest—4.5 mg/day—approved dose of pramipexole (Mirapex Package Insert; Revised July 2016).

In the report by Luo et al. (2016), although treatment of Parkinson patients with pramipexole at approved therapeutic doses significantly lowered the relative expression of alpha-synuclein (compared with pre-treatment values), the magnitude of the effect was small. Higher doses of pramipexole could have been more efficacious, but side effects such as vomiting and severe nausea preclude the use of higher doses. For example, Corrigan et al (2000) report that doses of 5 mg/day of pramipexole, hardly higher than the maximum recommended dose of 4.5 mg/day (Pramipexole FDA-approved package Insert) caused nausea in 76% of patients and vomiting in 39% of patients. Furthermore, 36% of patients were not able to complete the study, presumably because of intolerable GI adverse events.

US 2014/0024644 discloses a series of indole- (or indazole)-carboxylic acid esters or amides, esterified or N-substituted with azabicycloalkyl oxabicycloalkyl or oxaazabicycloalkyl groups, endowed with a 5HT3-antagonist activity and therefore useful for the treatment of a great number of diseases treatable by inhibition of the 5-HT3 receptor. In particular, this document enumerates a series of disorders that may be treated with a 5-HT3-antagonist: emesis, migraine, substance abuse and addiction, neurodegenerative and psychiatric disorders (including Parkinson's disease), gastrointestinal disorders, immunological disorders, atherosclerosis and inflammation. The document also discloses the possible combination of said 5HT3-antagonists with a great number of active agents including pramipexole, without any further information.

The present inventors, in a different therapeutic context, disclosed the possibility of increasing the doses of an acetylcholinesterase inhibitor by combining said acetylcholinesterase inhibitor with an antiemetic agent, including 5TH3-antagonists, in US 2011/0071135.

In conclusion, notwithstanding the massive existing literature, in particular Willner et al. 1994, Corrigan et al 2000, and the disclosures of US 2008/0014259, US 2011/0071135 and US 2014/0024644, nobody succeeded in safely increasing pramipexole efficacy, and pramipexole currently provides only marginal activity in the treatment of Parkinson's disease.

Thus, the problem of providing safe, chronic, effective treatment of a patient, suffering from a synucleinopathy, with pramipexole remains unresolved.

SUMMARY OF THE INVENTION

The present invention increases the therapeutic window for pramipexole, to safely enable its full neuroprotective efficacy to a degree that delays onset and/or slows symptom progression to a clinically significant extent in those with PD-like disorders.

It has now been found that a 5-HT3-antagonist, such as ondansetron or a pharmaceutically acceptable salt or solvate thereof, by reducing or even abrogating the GI side effects of high doses of pramipexole enables the synucleinopathy-modifying potential of pramipexole.

It has also been found that the combination of a 6-propylamino-4,5,6,7-tetrahydro-1,3-benzothiazole-2-amine with a 5-HT3-antagonist, such as ondansetron or a pharmaceutically acceptable salt or solvate thereof, acts by normalizing the otherwise abnormal ratio of monomeric to oligomeric synuclein species in plasma exosomes originating from the CNS.

It has further been found that, by using a 5-HT3 receptor antagonist, also referred to as 5-HT3 receptor inhibitor or simply 5HT3-antagonist, in constant combination with a 6-propylamino-4,5,6,7-tetrahydro-1,3-benzothiazole-2-amine, it is possible to treat a patient suffering from a synucleinopathy by maintaining a therapeutically effective 6-propylamino-4,5,6,7-tetrahydro-1,3-benzothiazole-2-amine or of a pharmaceutically acceptable salt or solvate thereof daily dose with minimal adverse effect.

In addition, it has been found that said 5HT3-antagonist allows the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the motor symptoms of Parkinson's disease. Consequently, an improvement of the conditions of a patient suffering from a synucleinopathy, in particular PD, Lewy body disease, parkinsonian disorders associated with glucocerebrosidase (GBA) mutations, and MSA is attained.

In particular, it has been found that the protective action of said 5HT3-antagonist makes it possible to increase the pramipexole daily dose up to at least four times and up to ten times the maximum recommended and approved dose, and even more.

The combination of a 5-HT3-antagonist, such as ondansetron or a pharmaceutically acceptable salt or solvate thereof, as Component (a), with 6-propylamino-4,5,6,7-tetrahydro'-1,3-benzothiazole-2-amine, as Component (b), acts in a way that leads to normalizing the abnormal ratio of monomeric to oligomeric synuclein species in plasma exosomes originating from the CNS of patients suffering from a synucleinopathy.

Thus, the present invention provides a combination of a 5HT3-antagonist with 6-propylamino-4,5,6,7-tetrahydro-1,3-benzothiazole-2-amine, for use for the treatment of synucleinopathies by acting in a way that tends to normalize the abnormal ratio of monomeric to oligomeric synuclein species in plasma exosomes originating from the CNS.

The invention also provides a method for treating a patient suffering from a synucleinopathy which comprises treating said patient with an effective daily dose of a 5HT3-antagonist in combination with a therapeutically effective daily dose of 6-propylamino-4,5,6,7-tetrahydro-1,3-benzothiazole-2-amine.

According to an embodiment, said 5HT3-antagonist and said 6-propylamino-4,5,6,7-tetrahydro-1,3-benzothiazole-2-amine are each formulated in a pharmaceutical composition in admixture with a pharmaceutical carrier and separately administered to the patient in need of treatment with said combination. According to another embodiment, said 5HT3-antagonist and the 6-propylamino-4,5,6,7-tetrahydro-1,3-benzothiazole-2-amine are mixed together and formulated in a pharmaceutical composition (fixed-dose combination), in admixture with a pharmaceutical carrier, to be administered to the patient in need of said treatment.

Any of the 5HT3-antagonists advantageously shown to be effective and preferably approved for preventing or treating nausea and vomiting following cancer chemotherapy may be used in combination with a dose of 6-propylamino-4,5,6,7-tetrahydro-1,3-benzothiazole-2-amine that is generally currently used for treating neurodegenerative diseases, or with a dose higher than the dose currently used for treating neurodegenerative diseases. The chronic use of this combination improves the symptoms of a synucleinopathy by concurrently mitigating or even eliminating the adverse effects induced by the S-enantiomer that is present in said 6-propylamino-4,5,6,7-tetrahydro-1,3-benzothiazole-2-amine.

As stated in the definitions, 6-propylamino-4,5,6,7-tetrahydro-1,3-benzothiazole-2-amine stands for the active principle per se, independently of the salt or solvate of said active principle.

Herein, the expressions "salts or solvates thereof" and "salts and solvates thereof", in reference to any of the cited 5HT3-antagonists or to 6-propylamino-4,5,6,7-tetrahydro-1, 3-benzothiazole-2-amine, indicates that the salt of any of said cited 5HT3-antagonists or of said 6-propylamino-4,5, 6,7-tetrahydro-1,3-benzothiazole-2-amine may be solvated with a solvent, normally water.

According to the present invention, preferably, the 5HT3-antagonists used are those approved for preventing or treating nausea and vomiting following cancer chemotherapy. In fact, surprisingly, 5-HT3 receptor inhibitors, known to block or treat nausea, vomiting, and diarrhea induced by chemotherapeutic drugs, have been shown, in particular when administered at high doses, to also block the gastro-intestinal side effects of the S-enantiomer contained in said 6-propylamino-4,5,6,7-tetrahydro-1,3-benzothiazole-2-amine without affecting its efficacy in treating said synucleinopathy.

This finding is surprising also, given the apparently simple solution found by the present inventors, because, notwithstanding the gravity of the illnesses and the fact that both the 5HT3-antagonists and the 6-propylamino-4,5,6,7-tetrahydro-1,3-benzothiazole-2-amine were two families of products in use during more than a decade, each in its own indication, to date nobody thought that, by combining an effective dose of 5HT3-antagonist with an effective dose of a 6-propylamino-4,5,6,7-tetrahydro-1,3-benzothiazole-2-amine, it would be possible to safely improve the conditions of patients suffering from a synucleinopathy, by also allowing an increase of the dose of the S-enantiomer contained in said 6-propylamino-4,5,6,7-tetrahydro-1,3-benzothiazole-2-amine therapeutic dose, in particular the dose of pramipexole dihydrochloride monohydrate.

More particularly, it has been found that, in the case of pramipexole dihydrochloride monohydrate, the combination of a 5HT3-antagonist with said pramipexole dihydrochloride monohydrate allows for the administration of a therapeutically effective pramipexole dose that, in many patients, will significantly exceed the maximum recommended dose (4.5 mg/day) of pramipexole dihydrochloride monohydrate for the treatment of the symptoms of PD, thus increasing its efficacy in the treatment of a patient suffering from a synucleinopathy such as PD, including unexpectedly and substantially slowing disease progression.

Thus, the present invention provides a method for treating a synucleinopathy, which comprises administering to a patient in need of said treatment an effective daily dose of a 5HT3-antagonist in combination with an effective daily dose of a 6-propylamino-4,5,6,7-tetrahydro-1,3-benzothiazole-2-amine.

According to the above definition, the expression "effective daily dose of pramipexole" refers to an effective pediatric or adult daily pramipexole dose corresponding (i.e. equivalent) to at least the pramipexole dihydrochloride monohydrate approved daily dose for the treatment of Parkinson's disease. However, it is hereby specified that the "effective daily dose of pramipexole", as defined above, in combination with a 5HT3-antagonist, allows for the safe administration of the pramipexole dihydrochloride monohydrate approved daily dose for the treatment of Parkinson's disease without any adverse effect, as well as allows for the safe administration of pramipexole dihydrochloride monohydrate daily doses that are higher and also much higher than said approved doses.

Normally, according to the present invention, the "effective pramipexole daily dose" is from 0.375 mg to 42 mg. In the case of a (R)/(S)-mixture, the "effective S-enantiomer daily dose" is from 0.375 mg to 42 mg and applies to the daily dose of (S)-enantiomer that is present in and, hence, administered with said (R)/(S)-mixture.

Pharmaceutically acceptable salts of 6-propylamino-4,5, 6,7-tetrahydro-1,3-benzothiazole-2-amine are also included in the present invention. Illustrative examples of these salts include acid addition salts with mineral acids such as hydrochloric acid, hydrobromic acid, hydriodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid, glutamic acid and the like. The solvation agent is generally water.

According to an embodiment, the invention provides a pharmaceutical combination comprising a 5HT3-antagonist Component (a), at a dose that is at least as high as the pediatric or adult dose shown to be effective or approved for the prevention or treatment of postoperative nausea and vomiting or for the prevention of the chemotherapy-induced nausea and vomiting, and an effective dose of a 6-propylamino-4,5,6,7-tetrahydro-1,3-benzothiazole-2-amine Component (b).

According to another embodiment, the invention provides a 5HT3-antagonist, in a pharmaceutical composition comprising, as an active ingredient, said 5HT3-antagonist in admixture with a pharmaceutical carrier or vehicle, to be administered in combination with 6-propylamino-4,5,6,7-tetrahydro-1,3-benzothiazole-2-amine, also in a pharmaceutical composition, in admixture with a pharmaceutical carrier or vehicle.

According to this embodiment, said 5HT3-antagonist is present in said composition, in an amount/unit form at least as high as the pediatric or adult dose/unit form approved for the prevention or treatment of postoperative nausea and vomiting or for the prevention of the chemotherapy-induced nausea and vomiting, in admixture with a pharmaceutical carrier, for use for preventing or curing the adverse effects of pramipexole in the treatment of Parkinson's disease. The amount of 5HT3-antagonist/unit dose in said composition is from 1 μg to 300 mg, According to the same embodiment, said 6-propylamino-4,5,6,7-tetrahydro-1,3-benzothiazole-2-amine is present, in said composition, in an amount/unit form of from 0.125 mg to 3000 mg. If said 6-propylamino-4,5,6,7-tetrahydro-1,3-benzothiazole-2-amine is pramipexole or a pharmaceutically acceptable salt thereof, said pramipexole or a pharmaceutically acceptable salt thereof is present in said composition in an amount equivalent to from 0.125 mg to 42 mg, from 0.125 mg to 20 mg, or from 1.5 mg to 20 mg, of pramipexole dihydrochloride monohydrate.

In particular, according to this embodiment the invention provides a pharmaceutical combination comprising, as Components, (a) a 5HT3-antagonist, in a pharmaceutical composition in dosage unit form comprising, as an active ingredient, said 5HT3-antagonist, selected from the group consisting of azasetron and pharmaceutically acceptable salts and solvates thereof, in particular its hydrochloride, in an amount/unit form equivalent to from 5 mg to 10 mg of azasetron hydrochloride; dolasetron and pharmaceutically acceptable salts and solvates thereof, in particular its mesylate monohydrate, in an amount/unit form equivalent to from 1.5 mg to 200 mg of dolasetron mesylate; granisetron and pharmaceutically acceptable salts and solvates thereof, in particular its hydrochloride, in an amount/unit form equivalent to from 0.5 mg to 2 mg granisetron base; ondansetron and pharmaceutically acceptable salts and solvates thereof, in particular its hydrochloride dihydrate, in an amount/unit form equivalent to from 2 mg to 32 mg, normally from 2 mg to 16 mg of ondansetron base; palonosetron and pharmaceutically acceptable salts and solvates thereof, in particular its hydrochloride, in an amount/unit form equivalent to from 0.1 mg to 2 mg, normally from 0.25 mg to 0.5 mg palonosetron base; ramosetron and pharmaceutically acceptable salts and solvates thereof, in particular its hydrochloride, in an amount/unit form equivalent to from 2.5 µg to 100 mcg, normally from 5 mcg to 20 µg of ramosetron hydrochloride; and tropisetron and pharmaceutically acceptable salts and solvates thereof, in particular its hydrochloride, in an amount/unit form equivalent to from 2.5 mg to 5 mg tropisetron base, in admixture with a pharmaceutical carrier or vehicle; and (b) pramipexole or a pharmaceutically acceptable salt or solvate thereof, in a pharmaceutical composition comprising, as an active ingredient, said pramipexole or pharmaceutically acceptable salt thereof, in an amount per unit form equivalent to from 0.125 mg to 42 mg, or from 0.125 mg to 20 mg of pramipexole dihydrochloride monohydrate, in admixture with a pharmaceutical carrier or vehicle.

For use especially at the beginning of the treatment, said pramipexole or pharmaceutically acceptable salt or solvate thereof Component (b) is preferably present in said composition in an amount equivalent to from 1.5 mg to 20 mg, from 1.6 mg to 20 mg, from 1.625 mg to 20 mg, from 3 mg to 20 mg, from more than 4.5 mg to 20 mg, from more than 6 mg to 20 mg, or from 6.5 mg to 20 mg of pramipexole dihydrochloride monohydrate.

For the administration of pramipexole at higher doses, said pramipexole may be present in said composition in an amount equivalent to a wider range selected from the group consisting of from more than 1.5 mg to 45 mg, from 1.6 mg to 45 mg, from 1.625 mg to 45 mg, from 3 mg to 45 mg, from more than 4.5 mg to 45 mg, from more than 6 mg to 45 mg, and from 6.5 mg to 45 mg. Preferably, said pramipexole may be present in said composition in an amount equivalent to a wider range selected from the group consisting of from more than 1.5 mg to 42 mg, from 1.6 mg to 42 mg, from 1.625 mg to 42 mg, from 3 mg to 42 mg, from more than 4.5 mg to 42 mg, from more than 6 mg to 42 mg, and from 6.5 mg to 42 mg.

In said combination, said pramipexole or pharmaceutically acceptable salt or solvate thereof may be present, in said pharmaceutical composition, in an amount per unit form equivalent to from 1.6 mg to 10 mg or from 6.5 mg to 10 mg of pramipexole dihydrochloride monohydrate, in admixture with a pharmaceutical carrier or vehicle for an immediate-release formulation. For the administration of pramipexole at higher doses, said amount per IR-unit form will be equivalent to from 1.6 mg to 21 mg or from 6.5 mg to 21 mg of pramipexole dihydrochloride monohydrate.

In said combination, said pramipexole or pharmaceutically acceptable salt or solvate thereof may also be present, in said pharmaceutical composition, in an amount per unit form equivalent to from more than 4.5 mg to 20 mg or from more than 6 mg to 20 mg, of pramipexole dihydrochloride monohydrate, in admixture with a pharmaceutical carrier or vehicle for an extended-release formulation. For the administration of pramipexole at higher doses, said amount per ER-unit form will be equivalent to from more than 4.5 mg to 45 mg or from 6.5 mg to 45 mg of pramipexole dihydrochloride monohydrate. Preferably, said amount per ER-unit form will be equivalent to from more than 4.5 mg to 42 mg or from 6.5 mg to 42 mg of pramipexole dihydrochloride monohydrate.

According to this embodiment, the invention also provides the above 5HT3-antagonist Component (a), in the above pharmaceutical composition, in the above dose per unit form, in admixture with a pharmaceutical carrier or vehicle, for the treatment of a synucleinopathy, in combination with the above 6-propylamino-4,5,6,7-tetrahydro-1,3-benzothiazole-2-amine Component (b), in the above pharmaceutical composition, in the above dose per unit form.

According to another aspect of this embodiment, the invention provides a pharmaceutical combination comprising (a) a 5HT3-antagonist, in a pharmaceutical composition comprising, as an active ingredient, said 5HT3-antagonist, in an amount at least as high as the dose/unit form approved for the prevention or treatment of postoperative nausea and vomiting or for the prevention of the chemotherapy-induced nausea and vomiting, in admixture with a pharmaceutical carrier or vehicle; and (b) pramipexole dihydrochloride monohydrate, in a pharmaceutical composition comprising, as an active ingredient, said pramipexole dihydrochloride monohydrate, in an amount/unit form at least as high as the dose/unit form approved for the treatment of Parkinson's disease, in admixture with a pharmaceutical carrier or vehicle.

In said combination, Component (a) is present in said composition in an amount of from 1 µg to 300 mg and pramipexole dihydrochloride monohydrate Component (b) is present in an amount of from 0.125 mg to 45 mg or from 1.5 to 22.5 mg. Preferably, Component (a) is present in said composition in an amount of from 1 µg to 300 mg and pramipexole dihydrochloride monohydrate Component (b) is present in an amount of from 0.125 mg to 42 mg or from 1.5 to 20 mg.

According to a further embodiment, the invention provides the use of a 5HT3-antagonist for the preparation of a medicament including a pharmaceutical composition comprising, as an active ingredient, said 5HT3-antagonist, in an amount/unit form at least as high as the pediatric or adult dose shown to be effective, or approved for the prevention or treatment of postoperative nausea and vomiting or for the prevention of the chemotherapy-induced nausea and vomiting, in admixture with a pharmaceutical carrier, for preventing or curing the adverse effects of a 6-propylamino-4,5,6,7-tetrahydro-1,3-benzothiazole-2-amine or of a pharmaceutically acceptable salt and/or solvate thereof, in the treatment of Parkinson's disease.

As set forth above, the amount/unit form of the 5HT3-antagonist is at least as high as the pediatric or adult dose shown to be effective, or approved for the prevention or treatment of postoperative nausea and vomiting or for the prevention of the chemotherapy-induced nausea and vomiting, and may be up to 6 times said dose.

According to yet a further embodiment, the invention provides a pharmaceutical fixed-dose combination including a pharmaceutical composition comprising a 5HT3-antagonist, in an amount/unit form that is at least as high as the pediatric or adult dose shown to be effective, or approved for the prevention and treatment of postoperative nausea and vomiting or for the prevention of the chemotherapy-induced nausea and vomiting, as Component (a) and an effective dose/unit form of 6-propylamino-4,5,6,7-tetrahydro-1,3-benzothiazole-2-amine, as Component (b), in admixture with a pharmaceutical carrier or vehicle.

The dose of the 6-propylamino-4,5,6,7-tetrahydro-1,3-benzothiazole-2-amine per IR-unit form will range from 1.5 mg to 1500 mg, depending on safety and tolerability (in combination with the 5HT3-antagonist). The above range may be included in a wider dose range comprising lower 6-propylamino-4,5,6,7-tetrahydro-1,3-benzothiazole-2-amine doses per IR unit form. Said 6-propylamino-4,5,6,7-tetrahydro-1,3-benzothiazole-2-amine wider dose range per unit form may be from 0.125 mg to 1500 mg, advantageously from 1.5 mg to 1500 mg, preferably from 1.6 mg to 1500 mg.

The dose of the 6-propylamino-4,5,6,7-tetrahydro-1,3-benzothiazole-2-amine, as a (R)/(S)-mixture, per IR-unit form will range from 50 mg to 1500 mg, depending on safety and tolerability (in combination with the 5HT3-antagonist). The above range is inclusive of a (S)-enantiomer amount of from 0.125 mg to 10 mg per IR-unit form. For the administration of pramipexole at higher doses, the above range will be from 0.125 mg to 21 mg, advantageously from 6.5 mg to 21 mg per IR-unit form.

Normally, if said 6-propylamino-4,5,6,7-tetrahydro-1,3-benzothiazole-2-amine is pramipexole dihydrochloride monohydrate, the dose-range is from 0.125 mg to 10 mg, advantageously from 1.5 mg to 10 mg or from 6.5 mg to 10 mg per IR-unit form, depending on safety and tolerability (in combination with the 5HT3-antagonist). For the administration of pramipexole at higher doses, said dose-range will be from 0.125 mg to 21 mg, normally from 6.5 mg to 21 mg.

If the 5HT3-antagonist is ondansetron hydrochloride dihydrate, the ondansetron dose per IR unit form, in combination with pramipexole dihydrochloride monohydrate, will be equivalent to from 2 mg to 32 mg, from 4 mg to 32 mg, or from 4 mg to 16 mg of ondansetron base.

The dose/unit form of 6-propylamino-4,5,6,7-tetrahydro-1,3-benzothiazole-2-amine in an ER formulation, including slow-release compositions and transdermal therapeutic systems such as transdermal patches, will range from 3 mg to 3000 mg, depending on the tolerability (in combination with the 5HT3-antagonist).

The dose/unit form of 6-propylamino-4,5,6,7-tetrahydro-1,3-benzothiazole-2-amine, as a (R)/(S)-mixture, in an ER formulation, including slow-release compositions and transdermal therapeutic systems such as transdermal patches, will be in a range from 150 mg to 3000 mg. normally from 300 mg to 3000 mg of pramipexole dihydrochloride monohydrate, inclusive of a (S)-enantiomer dose/unit form equivalent to from 0.375 mg to 45 mg, or from more than 6 mg to 45 mg of pramipexole dihydrochloride monohydrate; preferably, from 0.375 mg to 42 mg, or from more than 6 mg to 42 mg of pramipexole dihydrochloride monohydrate, depending on the tolerability (in combination with the 5HT3-antagonist).

Normally, if said 6-propylamino-4,5,6,7-tetrahydro-1,3-benzothiazole-2-amine is pramipexole dihydrochloride monohydrate, the dose-range/ER-unit form will be from 3 mg to 20 mg. Advantageously, if said 6-propylamino-4,5,6,7-tetrahydro-1,3-benzothiazole-2-amine is pramipexole or a pharmaceutically acceptable salt thereof, said dose-range/ER-unit form will be equivalent to from more than 4.5 mg to 45 mg or from more than 6 mg to 45 mg, in some cases from more than 4.5 mg to 22.5 mg, preferably from more than 6 mg to 22.5 mg or from 6.5 mg to 22.5 mg, of pramipexole dihydrochloride monohydrate. Preferably, said dose-range/ER-unit form will be equivalent to from more than 4.5 mg to 42 mg or from more than 6 mg to 42 mg, in some cases from more than 4.5 mg to 20 mg, preferably from more than 6 mg to 20 mg or from 6.5 mg to 20 mg, of pramipexole dihydrochloride monohydrate.

If the 5-HT3 antagonist is ondansetron, the dose/ER-unit form will range from 8 mg to 32 mg.

If the 5-HT3 antagonist is dolasetron, the dose/unit form in combination with 6-propylamino-4,5,6,7-tetrahydro-1,3-benzothiazole-2-amine, at the above doses/unit form, will range from 1.5 mg to 200 mg, preferably from 20 mg to 200 mg (in dolasetron mesylate).

Normally, in the method (or use) for the treatment of a synucleinopathy according to the present invention, the 6-propylamino-4,5,6,7-tetrahydro-1,3-benzothiazole-2-amine, normally in a pharmaceutical composition in admixture with a pharmaceutical carrier or vehicle, is administered to a patient in need of said treatment at a daily dose of from 1.5 mg to 3000 mg. In practice, said daily dose is selected from the group consisting of pramipexole or a pharmaceutically acceptable salt thereof, at a daily dose equivalent to from 1.5 mg to 42 mg of pramipexole dihydrochloride monohydrate;

the racemate or a pharmaceutically acceptable salt thereof, at a daily dose of from 3 mg to 84 mg of pramipexole dihydrochloride monohydrate (thus, obviously, including a daily dose of (S)-6-propylamino-4,5,6,7-tetrahydro-1,3-benzothiazole-2-amine equivalent to from 1.5 mg to 42 mg of pramipexole dihydrochloride monohydrate, and a daily dose of (R)-6-propylamino-4,5,6,7-tetrahydro-1,3-benzothiazole-2-amine equivalent to from 1.5 mg to 42 mg of pramipexole dihydrochloride monohydrate); and a (R)/(S)-mixture, at a daily dose of from 150 mg to 3000 mg, including a (S)-enantiomer daily dose equivalent to from 1.5 mg to 42 mg of pramipexole dihydrochloride monohydrate (thus, obviously, said daily dose being constituted by a dose of (S)-enantiomer equivalent to from 1.5 mg to 42 mg of pramipexole dihydrochloride monohydrate and by a (R)-6-propylamino-4,5,6,7-tetrahydro-1,3-benzothiazole-2-amine dose equivalent of from 150 mg to 3000 mg minus (from 1.5 to 42 mg) of pramipexole dihydrochloride monohydrate).

In the method (or use) for the treatment of a synucleinopathy according to the present invention, the 6-propylamino-4,5,6,7-tetrahydro-1,3-benzothiazole-2-amine, as a (R)/(S)-mixture, normally in a pharmaceutical composition in admixture with a pharmaceutical carrier or vehicle, is administered to a patient in need of said treatment at a daily dose of from 1.5 mg to 3000 mg or of from 3.0 mg to 3000 mg; inclusive of a (S)-enantiomer daily dose equivalent to from 0.375 mg to 45 mg, preferably inclusive of a (S)-enantiomer daily dose of from more than 6 mg to 45 mg or from 6.5 mg to 45 mg of pramipexole dihydrochloride monohydrate, and more preferably, inclusive of a (S)-enantiomer daily dose equivalent to from 0.375 mg to 42 mg, of from more than 6 mg to 42 mg or of from 6.5 mg to 42 mg of pramipexole dihydrochloride monohydrate.

In another embodiment, in the method (or use) for the treatment of a synucleinopathy according to the present invention, the 6-propylamino-4,5,6,7-tetrahydro-1,3-benzothiazole-2-amine, as a (R)/(S)-mixture, is in a slow-release pharmaceutical composition or transdermal therapeutic systems such as transdermal patches, and is administered to a patient in need of said treatment at a daily dose of from 150 mg to 3000 mg or of from 300 mg to 3000 mg, inclusive of a (S)-enantiomer daily dose equivalent to from 0.375 mg to 42 mg, preferably inclusive of a (S)-enantiomer daily dose of from more than 6 mg to 42 mg or from 6.5 mg to 42 mg of pramipexole dihydrochloride monohydrate. In said method (or use) according to the present invention, the 6-propylamino-4,5,6,7-tetrahydro-1,3-benzothiazole-2-amine is administered to said patient in combination with a 5HT3-antagonist. Due to the presence of the 5HT3-antagonist in the combination, advantageously said daily dose range may be inclusive of a (S)-enantiomer daily dose equivalent to from more than 4.5 mg to 42 mg, preferably from more than 6 mg to 42 mg of pramipexole dihydrochloride monohydrate.

According to a particular embodiment, in said method (or use), said 6-propylamino-4,5,6,7-tetrahydro-1,3-benzothiazole-2-amine is pramipexole dihydrochloride monohydrate that is administered to said patient at a daily dose from more than 4.5 mg to 42 mg, preferably—from more than 6 mg to 42 mg or from 6.5 mg to 42 mg. According to this embodiment, in said method (or use) the 6-propylamino-4,5,6,7-tetrahydro-1,3-benzothiazole-2-amine is administered to said patient in combination with a 5HT3-antagonist.

If the 5-HT3 antagonist is ondansetron, said ondansetron is administered to said patient, as ondansetron hydrochloride dihydrate, at a daily dose that is equivalent to from 4 mg to 32 mg of ondansetron base.

If the 5-HT3 antagonist is dolasetron, said dolasetron is administered to said patient as dolasetron mesylate monohydrate, at a daily dose from 1.5 mg to 200 mg, preferably at an oral dose of from 20 mg to 200 mg (in dolasetron mesylate).

Herein, the pramipexole dose ranges per unit form comprise the pramipexole effective doses currently used in the treatment of PD and also include low doses that can be administered especially in the case of the initial titration of the pramipexole daily dose. However, according to the present invention, the therapeutically effective pramipexole or a pharmaceutically acceptable salt or solvate thereof dose-regimen in the safe treatment of the synucleinopathies with the above-illustrated combination, including fixed-dose combinations, may be equivalent to more than 4.5 mg/day, and also to more than 6 mg/day (up to 45 mg/day) of pramipexole dihydrochloride monohydrate.

Thus, the invention also provides a new pharmaceutical compositions in dosage unit form comprising an active ingredient selected from the group consisting of
  a pramipexole or a pharmaceutically acceptable salt or solvates thereof dose, per IR-unit form, equivalent to from more than 6 mg to 21 mg of pramipexole dihydrochloride monohydrate; and
  pramipexole or a pharmaceutically acceptable salt or solvates thereof dose, per ER-unit form, equivalent to from more than 6 mg to 42 mg of pramipexole dihydrochloride monohydrate,
in admixture with a pharmaceutical carrier or vehicle.

The invention also provides a new pharmaceutical compositions in dosage unit form comprising an active ingredient selected from the group consisting of
  a pramipexole or a pharmaceutically acceptable salt or solvates thereof dose, per IR-unit form, equivalent to from more than 6 mg to 22.5 mg of pramipexole dihydrochloride monohydrate; and
  pramipexole or a pharmaceutically acceptable salt or solvates thereof dose, per ER-unit form, equivalent to from more than 6 mg to 45 mg of pramipexole dihydrochloride monohydrate,
in admixture with a pharmaceutical carrier or vehicle.

DETAILED DESCRIPTION

As summarized above, the present invention provides a combination, including fixed-dose combinations, of a 5HT3-antagonist Component (a) with 6-propylamino-4,5,6,7-tetrahydro-1,3-benzothiazole-2-amine Component (b), and its use for the treatment of a synucleinopathy in a patient. In particular, the invention provides
  a method for treating a patient suffering from a synucleinopathy which comprises treating said patient with a 5HT3-antagonist in combination with 6-propylamino-4,5,6,7-tetrahydro-1,3-benzothiazole-2-amine;
  a 5HT3-antagonist, for use in combination with 6-propylamino-4,5,6,7-tetrahydro-1,3-benzothiazole-2-amine in the treatment of a patient suffering from a synucleinopathy;
  the use of a 5HT3-antagonist for the preparation of a medicament for treating a synucleinopathy in a patient in need of said treatment, in combination with 6-propylamino-4,5,6,7-tetrahydro-1,3-benzothiazole-2-amine; and
  a fixed dose combination comprising a pharmaceutical composition in dosage unit form comprising a 5HT3-antagonist Component (a) and 6-propylamino-4,5,6,7-tetrahydro-1,3-benzothiazole-2-amine Component (b), in admixture with a pharmaceutical carrier or vehicle.

The 5HT3-Antagonist

As set forth above, any of the 5HT3-antagonists disclosed in the literature may be used in combination with a daily dose of the herein above defined 6-propylamino-4,5,6,7-tetrahydro-1,3-benzothiazole-2-amine.

The long-term use of this combination slows the progression of a synucleinopathic disorder by mitigating or even eliminating the adverse effects induced by pramipexole, as such or as (S)-enantiomer in the racemate or in a (R)//S)-mixture, and thereby enabling the use of high doses and thus more neuroprotective doses of pramipexole.

Said 5HT3-antagonist is normally selected among those shown to be effective in or approved for the prevention or treatment of postoperative nausea and vomiting or for the prevention of the chemotherapy-induced nausea and vomiting.

The 5HT3-antagonist is preferably selected from the group consisting of 5-methyl-2-[(4-methyl-1H-imidazol-5-yl)methyl]-2,3,4,5-tetrahydro-1H-pyrido[4,3-b]indol-1-one (alosetron) and pharmaceutically acceptable salts and solvates thereof, especially its hydrochloride, disclosed in U.S. Pat. No. 5,360,800; (D)-6-chloro,3,4-dihydro-4-methyl-3-oxo-N-(quinuclidinyl)-2H-1,4-benzoxazine-8-carboxamide (azasetron) and pharmaceutically acceptable salts and solvates thereof, especially its hydrochloride, disclosed in U.S. Pat. No. 4,892,872; [(1S,5R)-8-methyl-8-azabicyclo[3.2.1]octan-3-yl] 3,5-dichlorobenzoate (bemesetron, CAS: 40796-97-2); (10R)-10-[(2-methyl-1H-imidazol-1-yl)methyl]-5,6,9,10-tetrahydro-4H-pyrido(3,2,1-jk)carbazol-11-one (cilansetron) and pharmaceutically acceptable salts and solvates thereof, especially its hydrochloride monohydrate, disclosed in U.S. Pat. No. 4,939,136; (3R)-10-oxo-8-azatricyclo[5.3.1.03,8]undec-5-yl 1H-indole-3-carboxylate (dolasetron) and pharmaceutically acceptable salts and solvates thereof, especially its monomethanesulfonate monohydrate, disclosed in U.S. Pat. No. 4,906,755; (+)-(R)-8,9-dihydro-10-methyl-7-[(5-methylimidazol-4-yl)methyl]pyrido[1,2-a]indol-6(7H)-one (fabesetron) and pharmaceutically acceptable salts and solvates thereof, especially its hydrochloride or maleate, disclosed in U.S. Pat. No. 5,141,945; 1-methyl-N-((1R,3r,5S)-9-methyl-9-azabicyclo[3.3.1]nonan-3-yl)-1H-indazole-3-carboxamide (granisetron) and pharmaceutically acceptable salts and solvates thereof, especially its hydrochloride, disclosed in U.S. Pat. No. 4,886,808; 2,3-dihydro-N-(8-methyl-8-azabicyclo[3.2.1]oct-3-yl)-2-oxo-1H-benzimidazole-1-carboxamide (itasetron) and pharmaceutically acceptable salts and solvates thereof, especially its hydrochloride, disclosed in U.S. Pat. No. 5,223,511; 1-phenylmethyl-2-(1-piperazinyl)-1H-benzimidazole (lerisetron) and pharmaceutically acceptable salts and solvates thereof, specially its hydrochloride, disclosed in U.S. Pat. No. 5,256,665 and, in a transdermal preparation, in U.S. Pat. No. 6,136,807; 6-fluoro-5-methyl-2-[(5-methyl-1H-imidazol-4-yl)methyl]-2,3,4,5-tetrahydro-1H-pyrido[4,3-b]indol-1-one (lurosetron, CAS 128486-54-4) and pharmaceutically acceptable salts and solvates thereof, especially its mesylate (GR 87442 N); (±) 1,2,3,9-tetrahydro-9-methyl-3-[(2-methyl-H-imidazol-1-yl)methyl]-4H-carbazol-4-one (ondansetron) and pharmaceutically acceptable salts and solvates thereof, especially its hydrochloride dihydrate, disclosed in U.S. Pat. No. 4,695,578; (3aS)-2-[(S)-1-azabicyclo [2.2.2]oct-3-yl]-2,3,3a,4,5,6-hexahydro-1-oxo-1H-benz[de]isoquinoline (palonosetron) and pharmaceutically acceptable salts and solvates thereof, especially its hydrochloride, disclosed in U.S. Pat. No. 5,202,333; 1-methylindol-3-yl)-[(5R)-4,5,6,7-tetrahydro-3H-benzimidazol-5-yl] methanone (ramosetron) and pharmaceutically acceptable salts and solvates thereof, especially its fumarate, disclosed in U.S. Pat. No. 5,344,927; endo-N-(8-methyl-8-azabicyclo [3.2.1]oct-3-yl)-2,3-dihydro-3,3-dimethyl-indole-1-carboxamide (3,3-dimethyl-N-1αH,5αH-tropan-3α-yl-1-indolinecarboxamide, ricasetron, CAS 117086-68-7) and pharmaceutically acceptable salts and solvates thereof, especially its hydrochloride; the (3-endo)-8-methyl-8-azabicyclo [3.2.1]oct-3-yl ester of 1H-indole-3-carboxylic acid (3-tropanylindole-3-carboxylate, tropisetron) and pharmaceutically acceptable salts and solvates thereof, especially its hydrochloride, disclosed in U.S. Pat. No. 4,789,673; and 5-chloro-2,2-dimethyl-N-(8-methyl-8-azabicyclo [3.2.1]oct-3-yl)-2,3-dihydro-1-benzofuran-7-carboxamide (zatosetron) and pharmaceutically acceptable salts and solvates thereof, especially its maleate, disclosed in U.S. Pat. No. 5,563,148; the disclosures of all the US patents cited in this paragraph being incorporated herein in their entirety by reference in their entirety.

Advantageously, said 5HT3-antagonist is selected from the group consisting of azasetron and pharmaceutically salts and solvates thereof, dolasetron and pharmaceutically acceptable salts and solvates thereof, granisetron and pharmaceutically salts and solvates thereof, ondansetron and pharmaceutically salts and solvates thereof, palonosetron and pharmaceutically acceptable salts and solvates thereof, ramosetron and pharmaceutically acceptable salts and solvates thereof, and tropisetron and pharmaceutically salts and solvates thereof.

Illustrative examples of pharmaceutically acceptable salts of these advantageous 5HT3-antagonists include acid addition salts with mineral acids such as hydrochloric acid, hydrobromic acid, hydriodic acid, sulfuric acid, nitric acid, carbonic acid, phosphoric acid and the like and acid addition salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like. The solvation agent is generally water.

Antagonists of the 5HT3 receptor that are approved for the prevention or treatment of postoperative nausea and vomiting or for the prevention of the chemotherapy-induced nausea and vomiting are particularly useful according to the present invention. In particular, azasetron hydrochloride, commercially available in 10-mg tablets and in 10-mg vials for intravenous injection; dolasetron monomethanesulfonate monohydrate (also referred to as dolasetron mesylate), commercially available in 200-mg maximal dose tablets, and in 12.5 mg/0.625 ml vials; granisetron hydrochloride, commercially available in 2.24-mg maximal dose tablets; ondansetron hydrochloride dihydrate, commercially available in 10-mg maximal dose tablets and in a 2 mg/ml (in ondansetron base) solution available in 20-ml multidose vials; palonosetron hydrochloride, commercially available in 0.56-mg tablets and in 0.075 mg/1.5 ml or 0.25 mg/5 ml (in palonosetron base) vials; ramosetron hydrochloride, commercially available in 0.15 mg/ml for injection and in 0.1 mg oral tablets; and tropisetron hydrochloride, commercially available in 5.64-mg capsules, in 2.256 mg/2 ml vials for intravenous injection, and in 5.64-mg vials for intravenous or subcutaneous injection; are particularly advantageous 5HT3-antagonists.

According to the present invention, the 5HT3-antagonist is used in a pharmaceutical composition comprising, as an active ingredient, said 5HT3-antagonist in an amount per unit form of from 1 μg to 300 mg, in admixture with a pharmaceutical carrier or vehicle, and is administered at a daily dose of from 1 μg to 300 mg, in combination with 6-propylamino-4,5,6,7-tetrahydro-1,3-benzothiazole-2-amine, at a daily dose equivalent to from 0.375 mg to 3000 mg of pramipexole dihydrochloride monohydrate, in particular with pramipexole dihydrochloride monohydrate at a daily dose equivalent to from 0.375 mg to 45 mg, preferably at a daily dose equivalent to from 0.375 mg to 42 mg of pramipexole dihydrochloride monohydrate, and with fluoxetine at a daily dose equivalent to from 4 mg to 90 mg of fluoxetine base.

Thus, for example, an oral pharmaceutical composition according to the present invention to be chronically administered in combination with 6-propylamino-4,5,6,7-tetrahydro-1,3-benzothiazole-2-amine, may comprise a 5HT3-antagonist selected from the group consisting of azasetron and pharmaceutically acceptable salts and solvates thereof, in an amount per unit form equivalent to from 5 mg to 10 mg of azasetron hydrochloride, to be administered at a daily dose equivalent to from 15 mg to 40 mg of azasetron hydrochloride; dolasetron and pharmaceutically acceptable salts and solvates thereof, in an amount per unit form equivalent to from 25 mg to 200 mg of dolasetron mesylate, to be administered at a daily dose equivalent to from 75 mg to 200 mg of dolasetron mesylate; granisetron and pharmaceutically acceptable salts and solvates thereof, in an amount per unit form equivalent to from 0.5 mg to 2 mg granisetron base, to be administered at a daily dose equivalent to from 1.5 mg to 8 mg of granisetron base; ondansetron and pharmaceutically acceptable salts and solvates thereof, in an amount per unit form equivalent to from 0.5 mg to 16 mg, normally from 2 mg to 8 mg of ondansetron base, to be administered at a daily dose equivalent to from 6 mg to 64 mg, normally from 6 mg to 32 mg of ondansetron base;

palonosetron and pharmaceutically acceptable salts and solvates thereof, in an amount per unit form equivalent to from 0.25 mg to 0.5 mg of palonosetron base, to be administered at a daily dose equivalent to from 0.75 to 2 mg of palonosetron base; ramosetron and pharmaceutically acceptable salts and solvates thereof, in an amount per unit form equivalent to from 0.05 mg to 0.2 mg of ramosetron hydrochloride, to be administered at a daily dose equivalent to from 0.05 mg to 0.2 mg of ramosetron hydrochloride; and tropisetron and pharmaceutically acceptable salts and solvates thereof, in an amount per unit form equivalent to from 2.5 mg to 5 mg of tropisetron base, to be administered at a daily dose equivalent to from 7.5 mg to 20 mg of tropisetron base.

Preferably, said 5HT3-antagonist is selected from the group consisting of azasetron hydrochloride, in an amount per unit form equivalent to from 5 mg to 10 mg to be administered at a daily dose equivalent to from 15 mg to 40 mg of azasetron hydrochloride; dolasetron mesylate, in an amount per unit form equivalent to from 25 mg to 200 mg of dolasetron mesylate, to be administered at a daily dose equivalent to from 75 mg to 200 mg; granisetron hydrochloride, in an amount per unit form equivalent to from 0.5 mg to 2 mg granisetron base, to be administered at a daily dose equivalent to from 1.5 mg to 16 mg, normally of from 2 mg to 8 mg; ondansetron hydrochloride dihydrate, in an amount equivalent to from 0.5 mg to 32 mg, normally from 2 mg to 32 mg, from 2 mg to 16 mg or from 2 mg to 8 mg ondansetron base, to be administered at a daily dose equivalent to from 6 mg to 64 mg, normally from 6 to 32 mg of ondansetron base; palonosetron hydrochloride, in an amount equivalent to from 0.25 mg to 0.5 mg palonosetron base, to be administered at a daily dose equivalent to from 0.75 to 2 mg of palonosetron base; ramosetron hydrochloride, in an amount per unit form of from 0.05 mg to 02 mg, to be administered at a daily dose of from 0.05 mg to 0.2 mg; and tropisetron hydrochloride, in an amount equivalent to from 2.5 mg to 5 mg tropisetron base, to be administered at a daily dose equivalent to from 7.5 mg to 20 mg of tropisetron base.

A composition comprising a 5HT3-antagonist as illustrated above is destined to be administered to a patient suffering from a synucleinopathy, in combination with 6-propylamino-4,5,6,7-tetrahydro-1,3-benzothiazole-2-amine, also in a pharmaceutical composition in dosage unit form comprising said 6-propylamino-4,5,6,7-tetrahydro-1,3-benzothiazole-2-amine in an amount per unit form equivalent to from 0.125 mg to 3000 mg, in particular as a (R)/(S)-mixture, in an amount per unit form equivalent to from 50 mg to 3000 mg of pramipexole dihydrochloride monohydrate, said amount per unit form including a (S)-enantiomer amount equivalent to from 0.125 to 45 mg of pramipexole dihydrochloride monohydrate; as a racemate, in an amount equivalent to from 0.25 mg to 90 mg of pramipexole dihydrochloride monohydrate; or as pramipexole or a pharmaceutically acceptable salt thereof, in an amount equivalent to from 0.125 mg to 45 mg of pramipexole dihydrochloride monohydrate. Preferably, said amount per unit form includes a (S)-enantiomer amount equivalent to from 0.125 to 42 mg of pramipexole dihydrochloride monohydrate; as a racemate, in an amount equivalent to from 0.25 mg to 84 mg of pramipexole dihydrochloride monohydrate; or as pramipexole or a pharmaceutically acceptable salt thereof, in an amount equivalent to from 0.125 mg to 42 mg of pramipexole dihydrochloride monohydrate.

The pharmaceutical composition in dosage unit form comprising a 5HT3-antagonist as illustrated above may contain another active ingredient, in particular 6-propylamino-4,5,6,7-tetrahydro-1,3-benzothiazole-2-amine, co-formulated with said 5HT3-antagonist, in admixture with a pharmaceutical carrier or vehicle in a fixed-dose combination.

The 6-propylamino-4,5,6,7-tetrahydro-1,3-benzothiazole-2-amine

As set forth in the above definitions, the 6-propylamino-4,5,6,7-tetrahydro-1,3-benzothiazole-2-amine is selected from the group consisting of
pramipexole, i.e. (S)-6-propylamino-4,5,6,7-tetrahydro-1,3-benzothiazole-2-amine, and pharmaceutically acceptable salts and solvates thereof;
the racemate, i.e. (R,S)-6-propylamino-4,5,6,7-tetrahydro-1,3-benzothiazole-2-amine, and pharmaceutically acceptable salts and solvates thereof; and
a (S)/(R)-mixture, i.e. a mixture of (R)-6-propylamino-4,5,6,7-tetrahydro-1,3-benzothiazole-2-amine and (S)-6-propylamino-4,5,6,7-tetrahydro-1,3-benzothiazole-2-amine, normally in a pharmaceutical composition, for example as described in US 2008/0014259, containing a therapeutically effective amount of (S)-enantiomer, in admixture with a pharmaceutical carrier or vehicle.

Illustrative examples of pharmaceutically acceptable salts or solvates of 6-propylamino-4,5,6,7-tetrahydro-1,3-benzothiazole-2-amine are derived from inorganic or organic acids such as hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. The solvation solvent is normally water.

In the case of pramipexole or pharmaceutically acceptable salt or solvate thereof, pramipexole dihydrochloride monohydrate, commercially available, is the preferred 6-propylamino-4,5,6,7-tetrahydro-1,3-benzothiazole-2-amine. For example, stable pharmaceutical compositions comprising pramipexole dihydrochloride monohydrate, disclosed in WO 2012/0140604 and in WO 2008/122638, both incorporated herein by reference in their entirety; and sustained release compositions comprising pramipexole dihydrochloride monohydrate, disclosed in U.S. Pat. No. 8,399,016, incorporated herein by reference in its entirety, may be useful for the use in combination with a 5-HT3-antagonist for the treatment of a synucleinopathy.

The racemate and pramipexole, described in U.S. Pat. No. 4,886,812 the contents of which is incorporated herein by reference in its entirety, are each a useful 6-propylamino-4,5,6,7-tetrahydro-1,3-benzothiazole-2-amine for the treatment of a synucleinopathy in combination with a 5HT3-antagonist.

A (S)/(R)-mixture, i.e. a pharmaceutical composition comprising a therapeutically effective amount of (R)-6-propylamino-4,5,6,7-tetrahydro-1,3-benzothiazole-2-amine or pharmaceutically acceptable salts and solvates thereof and a therapeutically effective amount of (S)-6-propylamino-4,5,6,7-tetrahydro-1,3-benzothiazole-2-amine or pharmaceutically acceptable salts and solvates thereof, as disclosed in US 2008/0014259, the contents of which are incorporated herein by reference in their entirety, also is a 6-propylamino-4,5,6,7-tetrahydro-1,3-benzothiazole-2-amine useful for the treatment of a synucleinopathy.

For the treatment of synucleinopathies, in combination with a 5HT3-antagonist as illustrated in "The 5HT3-antagonist" section above, the 6-propylamino-4,5,6,7-tetrahydro-1,3-benzothiazole-2-amine is formulated in a pharmaceutical composition comprising said 6-propylamino-4,5,6,7-tetrahydro-1,3-benzothiazole-2-amine in an amount equivalent to from 0.125 mg to 3000 mg in admixture with a pharmaceutical carrier or vehicle. Said composition is administered to a patient in need of said treatment at daily dose of from 0.375 mg to 3000 mg in combination with a 5HT3-antagonist at a daily dose of from 1 μg to 300 mg.

According to the present invention, the 6-propylamino-4,5,6,7-tetrahydro-1,3-benzothiazole-2-amine is preferably selected from the group consisting of

- (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in a dose per unit form equivalent to from 0.125 mg to 45 mg of pramipexole dihydrochloride monohydrate, and preferably, from 0.125 mg to 42 mg of pramipexole dihydrochloride monohydrate;
- (R,S)-6-propylamino-4,5,6,7-tetrahydro-1,3-benzothiazole-2-amine (the racemate) and pharmaceutically acceptable salts an solvates thereof, in a dose per unit form equivalent to from 0.25 mg to 90 mg of pramipexole dihydrochloride monohydrate (thus, obviously, including a dose per unit form of (S)-6-propylamino-4,5,6,7-tetrahydro-1,3-benzothiazole-2-amine equivalent to from 0.125 mg to 45 mg of pramipexole dihydrochloride monohydrate, and a dose per unit form of (R)-6-propylamino-4,5,6,7-tetrahydro-1,3-benzothiazole-2-amine equivalent to from 0.125 mg to 45 mg of pramipexole dihydrochloride monohydrate), and preferably, from 0.25 mg to 84 mg of pramipexole dihydrochloride monohydrate (thus, obviously, including a dose per unit form of (S)-6-propylamino-4,5,6,7-tetrahydro-1,3-benzothiazole-2-amine equivalent to from 0.125 mg to 42 mg of pramipexole dihydrochloride monohydrate, and a dose per unit form of (R)-6-propylamino-4,5,6,7-tetrahydro-1,3-benzothiazole-2-amine equivalent to from 0.125 mg to 42 mg of pramipexole dihydrochloride monohydrate); and
- a (R)/(S)-mixture. i.e. a pharmaceutical composition in dosage unit form comprising 6-propylamino-4,5,6,7-tetrahydro-1,3-benzothiazole-2-amine, at a dose per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 45 mg of pramipexole dihydrate monohydrate (thus, obviously, said amount per unit form being constituted by an amount of (S)-enantiomer equivalent to from 0.125 mg to 45 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg to 3000 mg minus (from 0.125 to 45 mg) of pramipexole dihydrochloride monohydrate), and preferably, from 0.125 mg to 42 mg of pramipexole dihydrochloride monohydrate (thus, obviously, said amount per unit form being constituted by an amount of (S)-enantiomer equivalent to from 0.125 mg to 42 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg to 3000 mg minus (from 0.125 to 42 mg) of pramipexole dihydrochloride monohydrate).

In said unit forms, the amount of pramipexole or of (S)-enantiomer in the racemate or in the (R)/(S)-mixture, per unit form, is normally equivalent to from more than 1.5 mg to 45 mg, and preferably, from more than 1.5 mg to 42 mg, advantageously from more than 4.5 mg to 45 mg, and preferably from more than 4.5 mg to 42 mg, more advantageously from more than 6 mg to 45 mg, and preferably, from more than 6 mg to 42 mg, and even more advantageously from more than 6.5 mg to 45 mg, and preferably from 6.5 mg to 42 mg of pramipexole dihydrochloride monohydrate.

Thus, according to a first embodiment, the present invention provides appropriate pramipexole unit forms, normally a pharmaceutical composition in dosage unit form comprising an active ingredient selected form the group consisting of

- a pramipexole or a pharmaceutically acceptable salt or solvates thereof dose, per IR-unit form, equivalent to from more than 6 mg to 22.5 mg or from 6.5 to 22.5 mg of pramipexole dihydrochloride monohydrate, and preferably, from more than 6 mg to 21 mg or from 6.5 to 21 mg of pramipexole dihydrochloride monohydrate; and
- pramipexole or a pharmaceutically acceptable salt or solvates thereof dose, per ER-unit form, equivalent to from more than 6 mg to 45 mg or from 6.5 to 45 mg of pramipexole dihydrochloride monohydrate, and preferably, from more than 6 mg to 42 mg, or from 6.5 to 42 mg.

in admixture with a pharmaceutical carrier or vehicle.

According to a first aspect of this first embodiment, the invention provides a pharmaceutical composition in dosage unit form comprising, as an active ingredient, pramipexole or a pharmaceutically acceptable salt thereof in an amount per unit form, in pramipexole dihydrochloride monohydrate, selected from the group consisting of 6.5 mg, 7 mg, 8 mg, 9.5 mg, 10 mg, 12 mg, 14 mg, 15 mg, 17.5 mg, 21 mg, and 22.5 mg, in admixture with a pharmaceutical carrier or vehicle in an IR-formulation.

According to a second aspect of this first embodiment, the invention provides a pharmaceutical composition in dosage unit form comprising, as an active ingredient, pramipexole or a pharmaceutically acceptable salt thereof in an amount per unit form, in pramipexole dihydrochloride monohydrate, selected from the group consisting of 6.5 mg, 7 mg, 8 mg, 9.5 mg, 10 mg, 11 mg, 13.5 mg, 15 mg, 16.5 mg, 18 mg, 20 mg, 22.5 mg, 25 mg, 27 mg, 30 mg, 32 mg, 35 mg, 37 mg, 40 mg, 42 mg, and 45 mg in admixture with a pharmaceutical carrier or vehicle in an ER-formulation.

As set forth above, the daily dose of pramipexole or pharmaceutically acceptable salt thereof, according to the present invention, is equivalent to from 0.375 mg to 42 mg of pramipexole dihydrochloride monohydrate. Said daily dose-range includes:

- low doses, normally equivalents of currently approved doses of from 0.375 mg to 1.5 mg, administered to a patient suffering from a synucleinopathy, in combination with a 5HT3-antagonist, during the titration period at the beginning of the treatment;
- equivalents of currently approved doses, normally from 1.5 mg to 4.5 mg, safely administered to a patient, in combination with a 5HT3-antagonist, according to the current protocols; and, without producing adverse events due to the presence of said 5HT3-antagonist, equivalents of higher (normally from more than 4.5 mg to 6 mg) and even much higher (normally from more than 6 mg to 45 mg, and preferably, from more than 6 mg to 42 mg) doses capable of objectively improving the condition of said patient, and providing the neuroprotective activity preconized by studies in animal models.

According to a second embodiment, the present invention provides appropriate (R,S)-6-propylamino-4,5,6,7-tetrahydro-1,3-benzothiazole-2-amine (the racemate) unit forms, normally a pharmaceutical composition comprising an active ingredient selected form the group consisting of
  said racemate or a pharmaceutically acceptable salt or solvate thereof dose, per IR-unit form, equivalent to from more than 12 mg to 45 mg or from 13 mg to 45 mg, and preferably, from more than 12 mg to 42 mg or from 13 mg to 42 mg of pramipexole dihydrochloride monohydrate; and
  said racemate or a pharmaceutically acceptable salt or solvates thereof dose, per ER-unit form, equivalent to from more than 12 mg to 90 mg or from more than 13 mg to 90 mg, and preferably, from more than 12 mg to 84 mg, or from 13 to 84 mg of pramipexole dihydrochloride monohydrate,
in admixture with a pharmaceutical carrier or vehicle.

The daily dose of (R,S)-6-propylamino-4,5,6,7-tetrahydro-1,3-benzothiazole-2-amine or pharmaceutically acceptable salt thereof (the racemate), according to the present invention, is equivalent to from 0.75 mg to 90 mg, and preferably, from 0.75 mg to 84 mg of pramipexole dihydrochloride monohydrate.

According to a third embodiment, the present invention provides an appropriate (R)/(S)-mixture consisting of a pharmaceutical composition in dosage unit form comprising, as active ingredients, (R)-6-propylamino-4,5,6,7-tetrahydro-1,3-benzothiazole-2-amine and (S)-6-propylamino-4,5,6,7-tetrahydro-1,3-benzothiazole-2-amine, in a total amount per unit form of from 50 mg to 3000 mg, preferably of from 150 mg to 3000 mg, said total amount per unit form including a (S)-enantiomer amount equivalent to from more than 6 mg to 45 mg, and preferably, from more than 6 mg to 42 mg of pramipexole dihydrochloride monohydrate, in admixture with a pharmaceutical carrier or vehicle.

According to an aspect of this third embodiment, the present invention provides an appropriate (R)/(S)-mixture selected from the group consisting of
  a pharmaceutical composition in dosage unit form comprising, as active ingredients, (R)-6-propylamino-4,5,6,7-tetrahydro-1,3-benzothiazole-2-amine and (S)-6-propylamino-4,5,6,7-tetrahydro-1,3-benzothiazole-2-amine, in a total amount per unit form of from 50 mg to 1500 mg, preferably from 150 mg to 1500 mg, said total amount per unit form including a (S)-enantiomer amount equivalent to from more than 6 mg to 22.5 mg, and preferably, from more than 6 mg to 21 mg of pramipexole dihydrochloride monohydrate, in admixture with a pharmaceutical carrier or vehicle in an IR-formulation; and
  a pharmaceutical composition in dosage unit form comprising, as active ingredients, (R)-6-propylamino-4,5,6,7-tetrahydro-1,3-benzothiazole-2-amine and (S)-6-propylamino-4,5,6,7-tetrahydro-1,3-benzothiazole-2-amine, in a total amount per unit form of from 50 mg to 3000 mg, preferably from 150 mg to 3000 mg, said total amount per unit form including a (S)-enantiomer amount equivalent to from more than 6 mg to 45 mg, and preferably, from more than 6 mg to 42 mg of pramipexole dihydrochloride monohydrate, in admixture with a pharmaceutical carrier or vehicle in an ER-formulation.

The daily dose of said (R)/(S)-mixture is from 150 mg to 3000 mg, preferably from 300 mg to 3000 mg, said daily dose including a (S)-6-propylamino-4,5,6,7-tetrahydro-1,3-benzothiazole-2-amine daily dose equivalent to from 0.375 mg to 42 mg, advantageously from more than 6 mg to 45 mg, and preferably, from more than 6 mg to 42 mg, and even more advantageously from more than 6.5 mg to 45 mg, and preferably, from 6.5 mg to 42 mg of pramipexole dihydrochloride monohydrate.

According to a particular embodiment, said 6-propylamino-4,5,6,7-tetrahydro-1,3-benzothiazole-2-amine is pramipexole dihydrochloride monohydrate, formulated in a pharmaceutical composition in dosage unit form comprising, as an active ingredient, said pramipexole dihydrochloride monohydrate in an amount per unit form of from more than 6 mg to 42 mg or from 6.5 mg to 42 mg in admixture with a pharmaceutical carrier or vehicle. Said composition is destined to be administered to a patient suffering from a synucleinopathy at a daily dose of from more than 6 mg to 42 mg, in combination with a 5HT3-antagonist.

According to another particular embodiment, said 6-propylamino-4,5,6,7-tetrahydro-1,3-benzothiazole-2-amine is pramipexole dihydrochloride monohydrate, formulated in a pharmaceutical composition in dosage unit form comprising, as an active ingredient, said pramipexole dihydrochloride monohydrate in an amount per unit form of from more than 6 mg to 45 mg or from 6.5 mg to 45 mg in admixture with a pharmaceutical carrier or vehicle. Said composition is destined to be administered to a patient suffering from a synucleinopathy at a daily dose of from more than 6 mg to 45 mg, in combination with a 5HT3-antagonist.

Preferably, said 5HT3-antagonist is one of the approved 5HT3-antgonists illustrated in "The 5HT3-antagonist" section, in an amount per unit form as illustrated in said section, in particular embodiments ondansetron or a pharmaceutically acceptable salt or solvate thereof, or dolasetron or a pharmaceutically acceptable salt or solvate thereof.

First Aspect of the Invention

According to a first aspect, the present invention provides a method for safely slowing or even reversing disease progression of patients suffering from a synucleinopathy and treated with a 6-propylamino-4,5,6,7-tetrahydro-1,3-benzothiazole-2-amine, by concurrently and chronically administering to said patients a 5HT3-antagonist.

More particularly, the invention provides a method for treating a synucleinopathy in a patient, which comprises administering to said patient in need of said treatment an effective daily dose of a 5HT3-antagonist in combination with an effective daily dose of a 6-propylamino-4,5,6,7-tetrahydro-1,3-benzothiazole-2-amine or of a pharmaceutically acceptable salt or solvate thereof.

In carrying out the method of the present invention, the daily dose of these 5HT3-antagonists is at least as high as that preventing or treating nausea and vomiting in pediatric or adult patients undergoing a surgical operation or cancer chemotherapy according to the current protocols for said treatment or prevention. Said daily dose normally is from 1 µg to 300 mg.

As set forth above, the 6-propylamino-4,5,6,7-tetrahydro-1,3-benzothiazole-2-amine is selected from the group consisting of the racemate, pramipexole, and (R)/(S)-mixtures and pharmaceutically acceptable salts and solvates thereof.

The doses per unit form and the daily doses of the 6-propylamino-4,5,6,7-tetrahydro-1,3-benzothiazole-2-amine are illustrated above in "The 6-propylamino-4,5,6,7-tetrahydro-1,3-benzothiazole-2-amine" section. Said 6-propylamino-4,5,6,7-tetrahydro-1,3-benzothiazole-2-amine dose per unit form consists of or includes an (S)-isomer amount per unit form equivalent from 0.125 mg to 42 mg, preferably from more than 6 mg to 42 mg of pramipexole dihydrochloride monohydrate. Said 6-propylamino-4,5,6,7-tetrahydro-1,3-benzothiazole-2-amine daily dose consists of or includes an (S)-isomer daily dose equivalent to from 0.375 mg to 42 mg of pramipexole dihydrochloride monohydrate. Preferably, said 6-propylamino-4,5,6,7-tetrahydro-1,3-benzothiazole-2-amine daily dose consists of or includes a (S)-isomer therapeutically effective daily dose equivalent to from more than 6 mg to 42 mg of pramipexole dihydrochloride dihydrate.

Said 6-propylamino-4,5,6,7-tetrahydro-1,3-benzothiazole-2-amine dose per unit form may also consist of or include an (S)-isomer amount per unit form equivalent from 0.125 mg to 45 mg, preferably from more than 6 mg to 45 mg of pramipexole dihydrochloride monohydrate. Said 6-propylamino-4,5,6,7-tetrahydro-1,3-benzothiazole-2-amine daily dose consists of or includes an (S)-isomer daily dose equivalent to from 0.375 mg to 45 mg of pramipexole dihydrochloride monohydrate. Preferably, said 6-propylamino-4,5,6,7-tetrahydro-1,3-benzothiazole-2-amine daily dose consists of or includes a (S)-isomer therapeutically effective daily dose equivalent to from more than 6 mg to 45 mg of pramipexole dihydrochloride dihydrate.

According to an embodiment, the 6-propylamino-4,5,6,7-tetrahydro-1,3-benzothiazole-2-amine is selected from the group consisting of

- (S)-6-propylamino-4,5,6,7-tetrahydro-1,3-benzothiazole-2-amine (INN: pramipexole) and pharmaceutically acceptable salts thereof, in particular its dihydrochloride monohydrate (USAN: pramipexole hydrochloride), in a dose/unit form equivalent to from 0.125 mg to 20 mg of pramipexole dihydrochloride monohydrate, to be administered in a daily dose equivalent to from 0.375 mg to 20 mg, preferably from more than 6 mg to 20 mg or from 6.5 mg to 20 mg of pramipexole dihydrochloride monohydrate;
- (S)-6-propylamino-4,5,6,7-tetrahydro-1,3-benzothiazole-2-amine (INN: pramipexole) and pharmaceutically acceptable salts thereof, in particular its dihydrochloride monohydrate (USAN: pramipexole hydrochloride), in a dose/unit form equivalent to from 0.125 mg to 22.5 mg of pramipexole dihydrochloride monohydrate, to be administered in a daily dose equivalent to from 0.375 mg to 22.5 mg, preferably from more than 6 mg to 22.5 mg or from 6.5 mg to 22.5 mg of pramipexole dihydrochloride monohydrate;
- (R,S)-6-propylamino-4,5,6,7-tetrahydro-1,3-benzothiazole-2-amine (the racemate) and pharmaceutically acceptable salts thereof, in a dose/unit form of from 0.25 mg to 84 mg, said dose being inclusive of an S-enantiomer amount per unit form equivalent to from 0.125 mg to 42 mg, preferably from more than 12 mg to 42 mg or from 13 mg to 42 mg, of pramipexole dihydrochloride monohydrate, administered in a daily dose equivalent to from 0.375 mg to 42 mg, preferably from more than 12 mg to 42 mg or from 13 mg to 42 mg, of pramipexole dihydrochloride monohydrate; and
- a (S)/(R)-mixture that is a pharmaceutical composition in dosage unit form comprising 6-propylamino-4,5,6,7-tetrahydro-1,3-benzothiazole-2-amine, in a dose per unit form of from 50 mg to 3000 mg, preferably from 150 mg to 3000 mg, said dose being inclusive of an S-enantiomer amount per unit form equivalent to from 0.125 to 20 mg, preferably from more than 6 mg to 20 mg or from 6.5 mg to 20 mg, of pramipexole dihydrochloride monohydrate, administered at a daily dose of from 150 mg to 300 mg, preferably from 300 mg to 3000 mg or from 450 mg to 3000 mg, inclusive of a (S)-enantiomer daily dose equivalent to from 0.375 mg to 20 mg, preferably from more than 6 mg to 20 mg or from 6.5 mg to 20 mg, of pramipexole dihydrochloride monohydrate.

Normally, in the method (or use) for the treatment of a synucleinopathy according to the present invention, the 6-propylamino-4,5,6,7-tetrahydro-1,3-benzothiazole-2-amine, in a pharmaceutical composition in admixture with a pharmaceutical carrier or vehicle, is administered to a patient in need of said treatment at a daily dose of from 1.5 mg to 3000 mg. In said method (or use) the 6-propylamino-4,5,6,7-tetrahydro-1,3-benzothiazole-2-amine is administered to said patient in combination with a 5HT3-antagonist. As set forth above, said 6-propylamino-4,5,6,7-tetrahydro-1,3-benzothiazole-2-amine may be pramipexole, the racemate or a (R)/(S)-mixture.

For this administration, a 6-propylamino-4,5,6,7-tetrahydro-1,3-benzothiazole-2-amine selected from the group consisting of pramipexole, racemic 6-propylamino-4,5,6,7-tetrahydro-1,3-benzothiazole-2-amine, and (R)/(S)-mixture is formulated in a pharmaceutical composition in dosage unit from comprising the aforementioned, respective amount-range per unit form of each of them, each in admixture with a pharmaceutical carrier or vehicle. Said composition may be manufactured according to known technologies, for example as described in WO 2012/0140604, WO 2008/122638, US 2013/0116292, U.S. Pat. No. 7,285,669, and US 2008/0014259 (U.S. Pat. No. 8,017,598) patent documents, all the disclosures of which are incorporated herein by reference in their entirety.

According to an embodiment, said 5HT3-antagonist is selected from the group consisting of azasetron and pharmaceutically acceptable salts and solvates thereof, especially its hydrochloride, at a daily dose equivalent to from 15 mg to 20 of azasetron hydrochloride; dolasetron and pharmaceutically acceptable salts and solvates thereof, especially its mesylate monohydrate, at a daily dose equivalent to from 75 mg to 200 mg of dolasetron mesylate; granisetron and pharmaceutically acceptable salts and solvates thereof, especially its hydrochloride, at a daily dose equivalent to from 1.5 mg to 8 mg of granisetron base; ondansetron and pharmaceutically acceptable salts and solvates thereof, especially its hydrochloride dihydrate, at a daily dose equivalent to from 6 to 32 mg of ondansetron base; palonosetron and pharmaceutically acceptable salts and solvates thereof, especially its hydrochloride, at a daily dose equivalent to from 0.1 to 2 mg, preferably from 0.25 to 0.5 mg of palonosetron base; ramosetron and pharmaceutically acceptable salts and solvates thereof, especially its hydrochloride, at a daily dose equivalent to from 75 mcg to 100 mcg of ramosetron hydrochloride; and tropisetron and pharmaceutically acceptable salts and solvates thereof, especially its hydrochloride, at a daily dose equivalent to from 7.5 to 20 mg of tropisetron base; and said 6-propylamino-4,5,6,7-tetrahydro-1,3-benzothiazole-2-amine is pramipexole or a pharmaceutically acceptable salt thereof, at a daily dose equivalent to from 0.375 mg to 42 mg, in particular from more than 6 mg to 42 mg or from 6.5 to 42 mg of pramipexole dihydrochloride monohydrate, or said 6-propylamino-4,5,6,7-tetrahydro-1,3-benzothiazole-2-amine is pramipexole or a pharmaceutically acceptable salt thereof, at a daily dose equivalent to from 0.375 mg to 45 mg, in particular from more than 6 mg to 45 mg or from 6.5 to 45 mg of pramipexole dihydrochloride monohydrate.

Specifically, said 6-propylamino-4,5,6,7-tetrahydro-1,3-benzothiazole-2-amine is pramipexole or a pharmaceutically acceptable salt thereof, at a daily dose equivalent to from 0.375 mg to 20 mg, in particular from 1.5 mg to 20 mg, advantageously from 1.6 to 20 mg, more advantageously from more than 4.5 mg to 20 mg, preferably from more than 6 mg to 20 mg or from 6.5 to 20 mg of pramipexole dihydrochloride monohydrate.

Specifically, said 6-propylamino-4,5,6,7-tetrahydro-1,3-benzothiazole-2-amine is pramipexole or a pharmaceutically acceptable salt thereof, at a daily dose equivalent to from 0.375 mg to 22.5 mg, in particular from 1.5 mg to 22.5 mg, advantageously from 1.6 to 22.5 mg, more advantageously from more than 4.5 mg to 21 mg, preferably from more than 6 mg to 22.5 mg or from 6.5 to 22.5 mg of pramipexole dihydrochloride monohydrate.

According to an advantageous embodiment, in the method of the present invention the 5HT3-antagonist is ondansetron hydrochloride dihydrate and the 6-propylamino-4,5,6,7-tetrahydro-1,3-benzothiazole-2-amine or a pharmaceutically acceptable salt or solvate thereof is pramipexole dihydrochloride monohydrate.

According to a particular embodiment, in said method (or use), said 6-propylamino-4,5,6,7-tetrahydro-1,3-benzothiazole-2-amine is pramipexole dihydrochloride monohydrate that is administered to said patient at a daily dose of from 1.5 mg to 42 mg, in some cases from 1.5 mg to 20 mg. According to this embodiment, in said method (or use) the 6-propylamino-4,5,6,7-tetrahydro-1,3-benzothiazole-2-amine is administered to said patient in combination with a 5HT3-antagonist.

According to an advantageous aspect of this particular embodiment, pramipexole dihydrochloride monohydrate is in a pharmaceutical composition in dosage unit form comprising, as an active ingredient, said pramipexole dihydrochloride monohydrate in an amount per unit form comprising from more than 4.5 mg to 21 mg, preferably from more than 6 mg to 21 mg or from 6.5 mg to 21 mg, in admixture with a pharmaceutical carrier or vehicle in an IR-formulation. Said composition is administered to said patient, in combination with a 5HT3-antagonist, twice or three times per day, up to the maximum pramipexole dihydrochloride monohydrate daily dose of 42 mg.

Another advantageous aspect of this particular embodiment involves pramipexole dihydrochloride monohydrate in a pharmaceutical composition in dosage unit form comprising, as an active ingredient, said pramipexole dihydrochloride monohydrate in an amount per unit form comprising from more than 4.5 mg to 22.5 mg, preferably from more than 6 mg to 22.5 mg or from 6.5 mg to 22.5 mg, in admixture with a pharmaceutical carrier or vehicle in an IR-formulation. Said composition is administered to said patient, in combination with a 5HT3-antagonist, twice or three times per day, up to the maximum pramipexole dihydrochloride monohydrate daily dose of 45 mg.

According to another advantageous aspect of this particular embodiment, pramipexole dihydrochloride monohydrate is in a pharmaceutical composition in dosage unit form comprising, as an active ingredient, said pramipexole dihydrochloride monohydrate in an amount per unit form comprising from more than 4.5 mg to 42 mg, preferably from more than 6 mg to 42 mg, or from 6.5 mg to 42 mg, in admixture with a pharmaceutical carrier or vehicle in an ER-formulation. Said composition is administered to said patient once a day, in combination with a 5HT3-antagonist.

Another advantageous aspect of this particular embodiment involves pramipexole dihydrochloride monohydrate is in a pharmaceutical composition in dosage unit form comprising, as an active ingredient, said pramipexole dihydrochloride monohydrate in an amount per unit form comprising from more than 4.5 mg to 45 mg, preferably from more than 6 mg to 45 mg, or from 6.5 mg to 45 mg, in admixture with a pharmaceutical carrier or vehicle in an ER-formulation. Said composition is administered to said patient once a day, in combination with a 5HT3-antagonist.

Preferably, in the method for treating a synucleinopathy in a patient according to the present invention, said 5HT3-antagonist is ondansetron hydrochloride dihydrate, at an effective daily dose (in ondansetron) of from 4 mg to 32 mg and said 6-propylamino-4,5,6,7-tetrahydro-1,3-benzothiazole-2-amine or a pharmaceutically acceptable salt or solvate thereof is pramipexole dihydrochloride monohydrate, at an effective daily dose of from 1.5 mg to 42 mg, in some cases from 1.5 mg to 20 mg. More particularly, in said method, said pramipexole dihydrochloride monohydrate is administered to a patient suffering from a synucleinopathy at a therapeutically effective daily dose of from more than 6 mg to 42 mg or from 6.5 mg to 42 mg, in some cases from more than 6 mg to 20 mg or from 6.5 mg to 20 mg.

Second Aspect of the Invention

According to a second aspect, the invention provides a 5HT3-antagonist for use in combination with 6-propylamino-4,5,6,7-tetrahydro-1,3-benzothiazole-2-amine, in the treatment of a synucleinopathy in a patient in need of said treatment.

In particular, this second aspect of the present invention provides a 5HT3-antagonist, in an amount of from 1 µg to 300 mg, for use in combination with a daily dose of said 6-propylamino-4,5,6,7-tetrahydro-1,3-benzothiazole-2-amine of from 0.375 mg to 3000 mg, for the treatment of a synucleinopathy in a patient in need of said treatment.

According to an embodiment said 5HT3-antagonist, normally in an amount per unit form of from 1 µg to 300 mg, is for use in combination with 6-propylamino-4,5,6,7-tetrahydro-1,3-benzothiazole-2-amine, as a (R)/(S)-mixture, at a daily dose of from 50 to 3000 mg, from 150 mg to 3000 mg or from 300 mg to 3000 mg, said daily dose including a (S)-enantiomer dose equivalent to from 0.375 mg to 42 mg, preferably to from more than 6 mg to 42 mg or from 6.5 mg to 42 mg, of pramipexole dihydrochloride monohydrate.

Said 6-propylamino-4,5,6,7-tetrahydro-1,3-benzothiazole-2-amine may also be a racemate, at a daily dose equivalent to from 0.75 mg to 84 mg, preferably to from more than 12 mg to 42 mg or from 13 mg to 42 mg, of pramipexole dihydrochloride monohydrate.

Said 6-propylamino-4,5,6,7-tetrahydro-1,3-benzothiazole-2-amine may also be a racemate, at a daily dose equivalent to from 0.75 mg to 90 mg, preferably to from more than 12 mg to 45 mg or from 13 mg to 45 mg, of pramipexole dihydrochloride monohydrate.

Preferably, said 6-propylamino-4,5,6,7-tetrahydro-1,3-benzothiazole-2-amine is pramipexole or pharmaceutically acceptable salt or solvate thereof, at a daily dose equivalent to from 1.5 mg to 20 mg, advantageously from more than 4.5 mg to 20 mg, more advantageously from 4.8 mg to 20 mg, preferably from more than 6 mg to 20 mg of pramipexole dihydrochloride monohydrate.

According to this second aspect, the pharmaceutical combination comprises a 5HT3-antagonist, at a dose that is at least as high as the pediatric or adult dose shown effective or approved for the prevention or treatment of postoperative nausea and vomiting or for the prevention of the chemotherapy-induced nausea and vomiting, and an effective dose of 6-propylamino-4,5,6,7-tetrahydro-1,3-benzothiazole-2-amine.

Advantageously, in said combination, said 5HT3 antagonist is selected from the group consisting of azasetron and pharmaceutically salts and solvates thereof, dolasetron and pharmaceutically salts and solvates thereof, granisetron and pharmaceutically salts and solvates thereof, ondansetron and pharmaceutically salts and solvates thereof, palonosetron and pharmaceutically salts and solvates thereof, ramosetron and pharmaceutically acceptable salts and solvates thereof, and tropisetron and pharmaceutically salts and solvates thereof; and said 6-propylamino-4,5,6,7-tetrahydro-1,3-benzothiazole-2-amine is pramipexole or a pharmaceutically acceptable salt or solvate thereof, safely administered to a patient suffering from a synucleinopathy at a daily dose equivalent to from 0.375 mg to 42 mg, preferably at a therapeutically effective daily dose of from more than 6 mg to 42 mg or from 6.5 mg to 42 mg.

In said combination with said 5HT3-antagonist, pramipexole or a pharmaceutically acceptable salt thereof is in some cases administered to a patient suffering from a synucleinopathy at a daily dose equivalent to from 1.5 mg to 20 mg, from 1.6 mg to 20 mg, from 1.625 mg to 20 mg, from 3 mg to 20 mg, from more than 4.5 mg to 20 mg, from 4.8 mg to 20 mg, from more than 6 mg to 20 mg or from 6.5 mg to 20 mg of pramipexole dihydrochloride monohydrate.

For their administration for the treatment of synucleinopathies, the 5HT3-antagonist and the 6-propylamino-4,5,6,7-tetrahydro-1,3-benzothiazole-2-amine are each formulated in a pharmaceutical composition in admixture with a pharmaceutical carrier or vehicle.

In particular, according to this second aspect, the pharmaceutical combination comprises, as Components, (a) a 5HT3-antagonist, in a pharmaceutical composition in dosage unit form comprising, as an active ingredient, said 5HT3-antagonist, selected from the group consisting of azasetron and pharmaceutically acceptable salts and solvates thereof, in particular its hydrochloride, in an amount/unit form equivalent to from 5 mg to 10 mg of azasetron hydrochloride; dolasetron and pharmaceutically acceptable salts and solvates thereof, in particular its mesylate monohydrate, in an amount/unit form equivalent to from 1.5 mg to 200 mg of dolasetron mesylate; granisetron and pharmaceutically acceptable salts and solvates thereof, in particular its hydrochloride, in an amount/unit form equivalent to from 0.5 mg to 2 mg granisetron base; ondansetron and pharmaceutically acceptable salts and solvates thereof, in particular its hydrochloride dihydrate, in an amount/unit form equivalent to from 2 mg to 32 mg, normally from 2 mg to 16 mg of ondansetron base; palonosetron and pharmaceutically acceptable salts and solvates thereof, in particular its hydrochloride, in an amount/unit form equivalent to from 0.1 mg to 2 mg, normally from 0.25 mg to 0.5 mg palonosetron base; ramosetron and pharmaceutically acceptable salts and solvates thereof, in particular its hydrochloride, in an amount/unit form equivalent to from 2.5 μg to 100 μg, normally from 5 mcg to 20 mcg of ramosetron hydrochloride; and tropisetron and pharmaceutically acceptable salts and solvates thereof, in particular its hydrochloride, in an amount/unit form equivalent to from 2.5 mg to 5 mg tropisetron base, in admixture with a pharmaceutical carrier or vehicle; and (b) pramipexole or a pharmaceutically acceptable salt or solvate thereof, in a pharmaceutical composition comprising, as an active ingredient, said pramipexole or pharmaceutically acceptable salt thereof, in an amount per unit form equivalent to from 0.125 mg to 42 mg, normally from more than 1.5 mg to 42 mg, from more than 4.5 mg to 42 mg, from more than 6 mg to 42 mg or from 6.5 mg to 42 of pramipexole dihydrochloride monohydrate, or pramipexole or a pharmaceutically acceptable salt or solvate thereof, in a pharmaceutical composition comprising, as an active ingredient, said pramipexole or pharmaceutically acceptable salt thereof, in an amount per unit form equivalent to from 0.125 mg to 45 mg, normally from more than 1.5 mg to 45 mg, from more than 4.5 mg to 45 mg, from more than 6 mg to 42 mg or from 6.5 mg to 45 of pramipexole dihydrochloride monohydrate;

in admixture with a pharmaceutical carrier or vehicle.

The pharmaceutical compositions thus obtained are concurrently or sequentially administered to a patient suffering from a synucleinopathy.

The use according to the present invention is made under conditions illustrated herein above for carrying out the method of treatment.

Third Aspect of the Invention

According to a third aspect, the invention provides the use of a 5HT3-antagonist for the preparation of a medicament for the treatment of a synucleinopathy in a patient in need of said treatment, in combination with an effective dose of 6-propylamino-4,5,6,7-tetrahydro-1,3-benzothiazole-2-amine.

Any 5HT3-antagonist disclosed in "The 5HT3-amtagonist" section may be used for the preparation of said medicament to be administered to said patient in combination with an effective dose of the 6-propylamino-4,5,6,7-tetrahydro-1,3-benzothiazole-2-amine illustrated in "The 6-propylamino-4,5,6,7-tetrahydro-1,3-benzothiazole-2-amine" section Advantageously, said 5HT3 antagonist is selected from the group consisting of azasetron and pharmaceutically salts and solvates thereof, dolasetron and pharmaceutically salts and solvates thereof, granisetron and pharmaceutically salts and solvates thereof, ondansetron and pharmaceutically salts and solvates thereof, palonosetron and pharmaceutically salts and solvates thereof, ramosetron and pharmaceutically acceptable salts and solvates thereof, and tropisetron and pharmaceutically salts and solvates thereof; and the 6-propylamino-4,5,6,7-tetrahydro-1,3-benzothiazole-2-amine is pramipexole or a pharmaceutically acceptable salt or solvate thereof.

In combination with said 5HT3-antagonist in a pharmaceutical composition, pramipexole or a pharmaceutically acceptable salt thereof is safely administered to a patient suffering from a synucleinopathy at a daily dose equivalent to from 0.375 mg to 42 mg, advantageously from more than 4.5 mg to 42 mg, preferably from more than 6 mg to 42 mg or from 6.5 mg to 42 mg, or in some cases equivalent to from 1.5 mg to 20 mg, from 1.6 mg to 20 mg, from 1.625 mg to 20 mg, from 3 mg to 20 mg, from more than 4.5 mg, from 4.8 mg to 20 mg, from more than 6 mg to 20 mg or from 6.5 mg to 20 mg of pramipexole dihydrochloride monohydrate.

For their administration for the treatment of synucleinopathies, the 5HT3-antagonist and the 6-propylamino-4,5,6,7- tetrahydro-1,3-benzothiazole-2-amine are each formulated in a pharmaceutical composition in admixture with a pharmaceutical carrier or vehicle.

The pharmaceutical compositions thus obtained are concurrently or sequentially administered to a patient suffering from a synucleinopathy.

Thus, according to this third aspect, the present invention provides a 5HT3-antagonist in a pharmaceutical composition comprising, as an active ingredient, said 5HT3-antagonist in admixture with a pharmaceutical carrier or vehicle, to be administered, concurrently or sequentially, in combination with 6-propylamino-4,5,6,7-tetrahydro-1,3-benzothiazole-2-amine, also in a pharmaceutical composition, in admixture with a pharmaceutical carrier or vehicle, for the treatment of a synucleinopathy in a patient in need of said treatment.

According to this aspect, the 5HT3-antagonist is present, in said pharmaceutical composition, in an amount per unit form of from 1 μg to 300 mg, in admixture with a pharmaceutical carrier or vehicle; and, respectively, said 6-propylamino-4,5,6,7-tetrahydro-1,3-benzothiazole-2-amine is present in said composition in an amount of from 0.125 mg to 3000 mg, in admixture with a pharmaceutical carrier or vehicle. More particularly, the dosage, i.e. the dose of said 6-propylamino-4,5,6,7-tetrahydro-1,3-benzothiazole-2-amine per unit form is in the range of from 0.125 mg to 1500 mg, advantageously from 1.5 mg to 1500 mg, more advantageously from 1.6 mg to 1500, preferably from 1.625 mg to 1500 mg in an IR unit form, or in the range of from 3 mg to 3000 mg in an ER-unit form.

A preferred 5HT3-antagonist in said pharmaceutical composition, for its indication for the treatment of a synucleinopathy in combination with said 6-propylamino-4,5,6,7-tetrahydro-1,3-benzothiazole-2-amine, is selected from the group consisting of azasetron and pharmaceutically acceptable salts and solvates thereof, in particular its hydrochloride, in an amount/unit form equivalent to from 5 mg to 10 mg of azasetron hydrochloride; dolasetron and pharmaceutically acceptable salts and solvates thereof, in particular its mesylate monohydrate, in an amount/unit form equivalent to from 20 mg to 200 mg of dolasetron mesylate; granisetron and pharmaceutically acceptable salts and solvates thereof, in particular its hydrochloride, in an amount/unit form equivalent to from 0.5 mg to 2 mg granisetron base; ondansetron and pharmaceutically acceptable salts and solvates thereof, in particular its hydrochloride dihydrate, in an amount/unit form equivalent to from 2 mg to 32 mg, normally from 2 mg to 16 mg of ondansetron base; palonosetron and pharmaceutically acceptable salts and solvates thereof, in particular its hydrochloride, in an amount/unit form equivalent to from 0.1 mg to 2 mg, normally from 0.25 mg to 0.5 mg palonosetron base; ramosetron and pharmaceutically acceptable salts and solvates thereof, in particular its hydrochloride, in an amount/unit form equivalent to from 2.5 μg to 100 mcg of ramosetron hydrochloride; and tropisetron and pharmaceutically acceptable salts and solvates thereof, in particular its hydrochloride, in an amount/unit form equivalent to from 2.5 mg to 5 mg tropisetron base.

Said pharmaceutical composition, comprising said preferred 5HT3-antagonist, is concurrently or sequentially administered to a patient suffering from a synucleinopathy in combination with 6-propylamino-4,5,6,7-tetrahydro-1,3-benzothiazole-2-amine, preferably selected from the group consisting of pramipexole and pharmaceutically acceptable salts and solvates thereof, also in a pharmaceutical composition, comprising said pramipexole and pharmaceutically acceptable salts and solvates thereof in an amount per unit form equivalent to from 0.125 mg to 42 mg, normally to a range selected from the group consisting of from 1.5 to 42 mg, from 1.6 mg to 42 mg, from 1.625 to 42 mg, from 3 mg to 42 mg, from more than 4.5 mg to 42 mg, from more than 6 mg to 42 mg, and from 6.5 mg to 42 mg of pramipexole dihydrochloride monohydrate, in admixture with a pharmaceutical carrier or vehicle.

Said pharmaceutical composition, comprising said preferred 5HT3-antagonist, is concurrently or sequentially administered to a patient suffering from a synucleinopathy in combination with 6-propylamino-4,5,6,7-tetrahydro-1,3-benzothiazole-2-amine, preferably selected from the group consisting of pramipexole and pharmaceutically acceptable salts and solvates thereof, also in a pharmaceutical composition, comprising said pramipexole and pharmaceutically acceptable salts and solvates thereof in an amount per unit form equivalent to from 0.125 mg to 45 mg, normally to a range selected from the group consisting of from 1.5 to 45 mg, from 1.6 mg to 45 mg, from 1.625 to 45 mg, from 3 mg to 45 mg, from more than 4.5 mg to 45 mg, from more than 6 mg to 45 mg, and from 6.5 mg to 45 mg of pramipexole dihydrochloride monohydrate, in admixture with a pharmaceutical carrier or vehicle.

According to an embodiment, especially for use at the beginning of the treatment, said pramipexole in said pharmaceutical composition is present in an amount per unit form—equivalent to from 0.125 mg to 21 mg or from 0.125 mg to 20 mg of pramipexole dihydrochloride monohydrate, in admixture with a pharmaceutical carrier or vehicle. In particular, said amount per unit form in said composition is equivalent to a range selected from the group consisting of from 1.5 mg to 20 mg, from 1.6 mg to 20 mg, from 1.625 mg to 20 mg, from 3 mg to 20 mg, from more than 4.5 mg to 20 mg, from more than 6 mg to 20 mg, and from 6.5 mg to 20 mg of pramipexole dihydrochloride monohydrate.

More particularly, said amount of pramipexole or pharmaceutically acceptable salt thereof, in an IR-formulation, is equivalent to from 0.125 to 21 mg, advantageously equivalent to a range selected from the group consisting of from more than 1.5 mg to 21 mg, from 1.6 mg to 21 mg, from 1.625 mg to 21 mg, from 3 mg to 21 mg, from more than 4.5 mg to 21 mg, from more than 6 mg to 21 mg, and from 6.5 mg to 21 mg of pramipexole dihydrochloride monohydrate; and, in an ER-formulation, is equivalent to a range selected from the group consisting of from 3 mg to 42 mg, from more than 4.5 mg to 42 mg, from more than 6 mg to 42 mg, and from 6.5 mg to 42 mg of pramipexole dihydrochloride monohydrate.

A composition comprising the 5HT3-antagonist and 6-propylamino-4,5,6,7-tetrahydro-1,3-benzothiazole-2-aminen according to this third aspect is also destined to the treatment of a synucleinopathy with the 6-propylamino-4,5,6,7-tetrahydro-1,3-benzothiazole-2-amine as a (R)/(S)-mixture, at a daily dose of from 150 mg to 3000 mg, normally from 300 mg to 3000 mg, said daily dose being inclusive of a (S)-enantiomer daily dose equivalent to from 0.375 mg to 42 mg, preferably from more than 6 mg to 42 mg or from 6.5 mg to 42 mg of pramipexole dihydrochloride monohydrate, said 6-propylamino-4,5,6,7-tetrahydro-1,3-benzothiazole-2-amine also being in a pharmaceutical in dosage unit form, in admixture with a pharmaceutical carrier or vehicle.

The composition comprising the 5HT3-antagonist and 6-propylamino-4,5,6,7-tetrahydro-1,3-benzothiazole-2-aminen thus manufactured is also destined to the treatment of a synucleinopathy with the 6-propylamino-4,5,6,7-tetrahydro- 1,3-benzothiazole-2-amine as the racemate, at a daily dose equivalent to from 0.75 mg to 84 mg, preferably from more than 12 mg to 84 mg or from 13 mg to 84 mg of pramipexole dihydrochloride monohydrate, said 6-propylamino-4,5,6,7-tetrahydro-1,3-benzothiazole-2-amine also being in a pharmaceutical in dosage unit form, in admixture with a pharmaceutical carrier or vehicle.

These pharmaceutical compositions, constantly used in combination each other, allow for the first time the use of pramipexole for the substantial and efficacious treatment of a patient suffering from a synucleinopathy such as Parkinson's disease, Lewy body dementia, parkinsonian disorders associated with glucocerebrosidase (GBA) mutations, and multiple system atrophy.

If the 5HT3-antagonist is ondansetron, the dose per tablet, to be administered to a patient in combination with 6-propylamino-4,5,6,7-tetrahydro-1,3-benzothiazole-2-amine, will range from 2 mg to 16 mg, normally from 2 mg to 8 mg or from 4 mg to 8 mg.

Ondansetron may also be present in a composition for transdermal administration, subcutaneous administration, intravenous administration, in a slow-release composition, such as extended release tablets or capsules, or a combination product, for example as a Transdermal Drug Delivery System (TDDS) such as a patch, preferably a matrix patch like that described by Cho J-R et al 2016; a patch pump, an infusion pump, or a micropump; or a fast-dissolving buccal film such as that described by Koland M et al. 2013.

In the treatment of synucleinopathies, the 5HT3-antagonist and the 6-propylamino-4,5,6,7-tetrahydro-1,3-benzothiazole-2-amine are used in combination and the two active components may be co-administered simultaneously or sequentially, or in a fixed dose combination including a pharmaceutical composition comprising the 5HT3-antagonist and 6-propylamino-4,5,6,7-tetrahydro-1,3-benzothiazole-2-amine, in admixture with a pharmaceutically acceptable carrier or vehicle.

The 5HT3-antagonist Component (a) and the 6-propylamino-4,5,6,7-tetrahydro-1,3-benzothiazole-2-amine Component (b) can be administered separately or together in any conventional oral or parenteral dosage unit form such as capsule, tablet, powder, cachet, suspension, solution, or transdermal device.

In the case of separate (concurrent or sequential) administration of said 5HT3-antagonist, in an effective amount per unit form, and of said 6-propylamino-4,5,6,7-tetrahydro-1,3-benzothiazole-2-amine, in an effective amount per unit form, each of them can be packaged in a kit comprising said 5HT3-antagonist, in admixture with a pharmaceutical carrier or vehicle, in a container; and said 6-propylamino-4,5,6,7-tetrahydro-1,3-benzothiazole-2-amine, preferably pramipexole, in admixture with a pharmaceutical carrier or vehicle, in another, separate container.

For the intended use in the treatment of synucleinopathies in combination with 6-propylamino-4,5,6,7-tetrahydro-1,3-benzothiazole-2-amine, the 5HT3-antagonist is formulated in a pharmaceutical composition, wherein said 5HT3-antagonist is in admixture with a pharmaceutical carrier or vehicle.

For their concurrent administration for the treatment of synucleinopathies, said 5HT3-antagonist and said 6-propylamino-4,5,6,7-tetrahydro-1,3-benzothiazole-2-amine, preferably pramipexole, may also be formulated together and with a pharmaceutical carrier or vehicle, in a pharmaceutical composition (fixed-dose combination).

Fourth Aspect of the Invention

According to a fourth aspect, the present invention provides pharmaceutical compositions including, as one of their active ingredients, an effective amount of a 5HT3-antagonist, as shown above, or of one of its pharmaceutically acceptable salts and solvates; and, as a second active ingredient, an effective amount of a 6-propylamino-4,5,6,7-tetrahydro-1,3-benzothiazole-2-amine or a pharmaceutically acceptable salt and/or solvate thereof, in admixture with a pharmaceutical carrier or vehicle.

Said 5HT3-antagonist and said 6-propylamino-4,5,6,7-tetrahydro-1,3-benzothiazole-2-amine are formulated together in a fixed-dose combination consisting of a pharmaceutical composition comprising said 5HT3-antagonist Component (a) and said 6-propylamino-4,5,6,7-tetrahydro-1,3-benzothiazole-2-amine Component (b), in admixture with a pharmaceutical carrier or vehicle.

The fixed-dose combinations assure the safe, concurrent administration of the 5HT3-antagonist and of the 6-propylamino-4,5,6,7-tetrahydro-1,3-benzothiazole-2-amine.

The dose per unit form of the 5HT3-antagonist Component (a) ranges from 1 μg to 300 mg; and the dose per unit form of the 6-propylamino-4,5,6,7-tetrahydro-1,3-benzothiazole-2-amine Component (b) ranges from 0.125 mg to 3000 mg.

In particular, according to this first aspect, the invention provides a pharmaceutical composition in dosage unit form which comprises (a) a 5HT3-antagonist, in an amount per unit form of from 1 μg to 300 mg; and
(b) a 6-propylamino-4,5,6,7-tetrahydro-1,3-benzothiazole-2-amine selected from the group consisting of the racemate or a pharmaceutically acceptable salt thereof, in an amount per unit form equivalent to from 0.25 mg to 84 mg of pramipexole dihydrochloride monohydrate; pramipexole or a pharmaceutically acceptable salt thereof, in an amount equivalent to from 0.125 mg to 42 mg of pramipexole dihydrochloride monohydrate; and a (R)/(S)-mixture, in an amount per unit form of from 50 mg to 3000 mg, inclusive of a (S)-enantiomer amount per unit form equivalent to from 0.125 mg to 42 mg of pramipexole dihydrochloride monohydrate, or a 6-propylamino-4,5,6,7-tetrahydro-1,3-benzothiazole-2-amine selected from the group consisting of the racemate or a pharmaceutically acceptable salt thereof, in an amount per unit form equivalent to from 0.25 mg to 90 mg of pramipexole dihydrochloride monohydrate; pramipexole or a pharmaceutically acceptable salt thereof, in an amount equivalent to from 0.125 mg to 45 mg of pramipexole dihydrochloride monohydrate; and a (R)/(S)-mixture, in an amount per unit form of from 50 mg to 3000 mg, inclusive of a (S)-enantiomer amount per unit form equivalent to from 0.125 mg to 45 mg of pramipexole dihydrochloride monohydrate;

in admixture with a pharmaceutical carrier or vehicle.

Preferably, the amount/unit form of the 5HT3-antagonist is at least as high as the pediatric or adult dose shown effective or approved for the prevention or treatment of postoperative nausea and vomiting or for the prevention of the chemotherapy-induced nausea and vomiting and may be up to 6 times said dose.

In particular, according to a first embodiment, the present invention provides a fixed-dose combination consisting of a pharmaceutical composition in dosage unit form which comprises, as Component (a), a 5 HT3-antagonist selected form the group consisting of azasetron and pharmaceutically acceptable salts and solvates thereof, in particular its hydrochloride, in an amount/unit form equivalent to from 5 mg to 10 mg of azasetron hydrochloride; dolasetron and pharmaceutically acceptable salts and solvates thereof, in particular its mesylate monohydrate, in an amount/unit form (in dolasetron mesylate) of from 20 mg to 200 mg; granisetron and pharmaceutically acceptable salts and solvates thereof, in particular its hydrochloride, in an amount/unit form equivalent to from 0.5 mg to 2 mg granisetron base; ondansetron and pharmaceutically acceptable salts and solvates thereof, in particular its hydrochloride dihydrate, in an amount/unit form equivalent to from 2 mg to 32 mg, normally from 2 mg to 16 mg of ondansetron base; palonosetron and pharmaceutically acceptable salts and solvates thereof, in particular its hydrochloride, in an amount/unit form equivalent to from 0.1 mg to 2 mg, normally from 0.25 mg to 0.5 mg palonosetron base; ramosetron and pharmaceutically acceptable salts and solvates thereof, in particular its hydrochloride, in an amount/unit form equivalent to from 2.5 μg to 100 mcg of ramosetron hydrochloride; and tropisetron and pharmaceutically acceptable salts and solvates thereof, in particular its hydrochloride, in an amount/unit form equivalent to from 2.5 mg to 5 mg tropisetron base; and, as Component (b), 6-propylamino-4,5,6,7-tetrahydro-1,3-benzothiazole-2-amine, in an amount/unit for of from 0.125 mg to 3000 mg, in admixture with a pharmaceutical carrier or vehicle.

Preferably, in said pharmaceutical composition, said 5HT3-antagonist is ondansetron hydrochloride dihydrate, in an amount per unit for equivalent to from 2 mg to 32 mg of ondansetron base and said 6-propylamino-4,5,6,7-tetrahydro-1,3-benzothiazole-2-amine is pramipexole dihydrochloride monohydrate, in an amount per unit form of from 0.125 mg to 42 mg or in an amount per unit form of from 0.125 mg to 45 mg.

More particularly, the dose of the 6-propylamino-4,5,6,7-tetrahydro-1,3-benzothiazole-2-amine Component (b) per IR-unit form normally is from 0.125 mg to 1500 mg, advantageously from 1.6 mg to 1500 mg preferably from 1.625 mg to 1500 mg, depending on safety and tolerability [in combination with the 5HT3-antagonist Component (a)].

Said dose of the 6-propylamino-4,5,6,7-tetrahydro-1,3-benzothiazole-2-amine per IR-unit form will normally range from 1.5 mg to 1500 mg depending on safety and tolerability (in combination with the 5HT3-antagonist).

According to this first embodiment, if said 6-propylamino-4,5,6,7-tetrahydro-1,3-benzothiazole-2-amine Component (b) of the fixed-dose combination is pramipexole or a pharmaceutically acceptable salt or solvate thereof, the dose-range per unit form is equivalent to from 0.125 mg to 42 mg, normally to a range selected from the group consisting of from 1.5 to 42 mg, from 1.6 mg to 42 mg, from 1.625 to 42 mg, from 3 mg to 42 mg, from more than 4.5 mg to 42 mg, from more than 6 mg to 42 mg, and from 6.5 mg to 42 mg of pramipexole dihydrochloride monohydrate, depending on safety and tolerability, in combination with the 5HT3-antagonist.

In some cases, especially for use at the beginning of the treatment, according to this first embodiment said pramipexole in said pharmaceutical composition is present in an amount per unit from equivalent to from 0.125 mg to 21 mg or in a dose-range per unit form equivalent to from 0.125 mg to 10 mg, advantageously from 1.5 mg to 10 mg, more advantageously from 1.6 mg to 10 mg, preferably from 1.625 mg to 10 mg of pramipexole dihydrochloride monohydrate, depending on safety and tolerability, in combination with the 5HT3-antagonist.

If the 6-propylamino-4,5,6,7-tetrahydro-1,3-benzothiazole-2-amine Component (b) of the fixed-dose combination is a (R)/(S)-mixture, the dose-range per unit form will be from 50 mg to 3000 mg, inclusive of a (S)-enantiomer amount per unit form equivalent to from 0.125 mg to 42 mg of pramipexole dihydrochloride monohydrate.

The dose of the 6-propylamino-4,5,6,7-tetrahydro-1,3-benzothiazole-2-amine, as (R)/(S)-mixture, per IR-unit form will range from 1.5 mg to 1500 mg, depending on safety and tolerability (in combination with the 5HT3-antagonist). The above range may be included in a wider dose range comprising lower 6-propylamino-4,5,6,7-tetrahydro-1,3-benzothiazole-2-amine doses per IR unit form. Said 6-propylamino-4,5,6,7-tetrahydro-1,3-benzothiazole-2-amine wider dose range per unit form may be from 0.125 mg to 1500 mg, advantageously from 1.5 mg to 1500 mg, preferably from 1.6 mg to 1500 mg. In particular, the dose of the 6-propylamino-4,5,6,7-tetrahydro-1,3-benzothiazole-2-amine, as (R)/(S)-mixture, per IR-unit form will range from 50 mg to 1500 mg, inclusive of an (S)-enantiomer amount equivalent to from 0.125 mg to 21 mg of pramipexole dihydrochloride monohydrate, depending on safety and tolerability (in combination with the 5HT3-antagonist).

If said 6-propylamino-4,5,6,7-tetrahydro-1,3-benzothiazole-2-amine is pramipexole, the dose-range per IR-unit form is equivalent to from 0.125 mg to 21 mg, preferably from more than 6 mg to 21 mg or from 6.5 mg to 21 mg of pramipexole dihydrochloride monohydrate, depending on safety and tolerability (in combination with the 5HT3-antagonist).

Normally, if said 6-propylamino-4,5,6,7-tetrahydro-1,3-benzothiazole-2-amine is pramipexole dihydrochloride monohydrate, the dose-range is from 0.125 mg to 10 mg, advantageously from 1.5 mg to 10 mg per IR-unit form, depending on safety and tolerability (in combination with the 5HT3-antagonist). If the 5HT3-antagonist is ondansetron hydrochloride dihydrate, the ondansetron dose per IR unit form, in combination with pramipexole dihydrochloride monohydrate, will be equivalent to from 2 mg to 16 mg or from 4 mg to 16 mg of ondansetron base. The above pramipexole dihydrochloride monohydrate dose range may be included in a wider dose range comprising lower pramipexole dihydrochloride monohydrate doses per IR unit form. Said pramipexole dihydrochloride monohydrate wider dose range per unit form may be from 0.125 mg to 10 mg, from 1.5 mg to 10 mg, from 1.6 mg to 10 mg, or from 1.625 mg to 10 mg per IR-unit form.

The dose/unit form of 6-propylamino-4,5,6,7-tetrahydro-1,3-benzothiazole-2-amine in an ER formulation, including slow-release compositions and transdermal therapeutic systems such as transdermal patches, will range from 3 mg to 3000 mg, depending on the tolerability (in combination with the 5HT3-antagonist).

If said 6-propylamino-4,5,6,7-tetrahydro-1,3-benzothiazole-2-amine is pramipexole, the dose-range/ER-unit form will be equivalent to from 1.5 mg to 42 mg of pramipexole dihydrochloride monohydrate. Advantageously, if said 6-propylamino-4,5,6,7-tetrahydro-1,3-benzothiazole-2-amine is pramipexole, said dose-range/ER-unit form will be equivalent to a range selected from the group consisting of from more than 4.5 mg to 42 mg, preferably from more than 6 mg to 42 mg and from 6.5 mg to 42 mg of pramipexole dihydrochloride monohydrate.

Normally, if said 6-propylamino-4,5,6,7-tetrahydro-1,3-benzothiazole-2-amine is pramipexole dihydrochloride monohydrate, the dose-range/ER-unit form will be from 1.5 mg to 20 mg, normally from 3 mg to 20 mg. Advantageously, if said 6-propylamino-4,5,6,7-tetrahydro-1,3-benzothiazole-2-amine is pramipexole or a pharmaceutically acceptable salt thereof, said dose-range/ER-unit form will be equivalent to from more than 4.5 mg to 20 mg, preferably from more than 6 mg to 20 mg of pramipexole dihydrochloride monohydrate.

If the 5-HT3 antagonist is ondansetron, the dose/ER-unit form will range from 4 mg to 32 mg or from 8 mg to 32 mg.

If the 5-HT3 antagonist is dolasetron, the dose/unit form in combination with 6-propylamino-4,5,6,7-tetrahydro-1,3-benzothiazole-2-amine, at the above doses/unit form, will range from 1.5 mg to 200 mg, preferably from 20 mg to 200 mg (in dolasetronmesylate).

According to this first embodiment, if said 6-propylamino-4,5,6,7-tetrahydro-1,3-benzothiazole-2-amine Component (b) of the fixed-dose combination is a (R)/(S)-mixture in an ER formulation, including slow-release compositions and transdermal therapeutic systems such as transdermal patches, said dose-range/ER-unit will be from 150 mg to 3000 mg, advantageously from 300 mg to 3000 mg, inclusive of a (S)-enantiomer amount per unit form equivalent to from 3 mg to 42 mg, preferably from more than 6 mg to 42 or from 6.5 mg to 42 mg of pramipexole dihydrochloride monohydrate, depending on the tolerability (in combination with the 5HT3-antagonist).

According to this first embodiment, if said 6-propylamino-4,5,6,7-tetrahydro-1,3-benzothiazole-2-amine Component (b) of the fixed-dose combination is the racemate, said dose-range/ER-unit form will be equivalent to a range selected from the group consisting of from more than 9 mg to 42 mg, preferably from more than 12 mg to 42 mg and from 13 mg to 42 mg of pramipexole dihydrochloride monohydrate.

According to yet a further embodiment, the invention provides a pharmaceutical fixed-dose combination consisting of a pharmaceutical composition comprising a 5HT3-antagonist, in an amount/unit form that is at least as high as the pediatric or adult dose shown to be effective or approved for the prevention and treatment of postoperative nausea and vomiting or for the prevention of the chemotherapy-induced nausea and vomiting, as Component (a) and an effective dose/unit form of a 6-propylamino-4,5,6,7-tetrahydro-1,3-benzothiazole-2-amine, as Component (b), in admixture with a pharmaceutical carrier or vehicle.

An advantageous pharmaceutical composition according to this fourth aspect of the invention comprises:
(a) a 5HT3-antagonist, in an amount at least as high as the pediatric or adult dose shown to be effective or approved for the prevention and treatment of postoperative nausea and vomiting or for the prevention or treatment of chemotherapy-induced nausea and vomiting; and
(b) pramipexole dihydrochloride monohydrate, in an amount at least at least as high as the dose approved for the treatment of Parkinson's disease,
in admixture with a pharmaceutical carrier or vehicle.

A preferred pharmaceutical composition according to this further aspect of the invention comprises:
(a) a 5HT3-antagonist selected from the group consisting of ondansetron and pharmaceutically acceptable salts thereof, in an amount, in ondansetron, of from 2 mg to 32 mg, from 4 mg to 32 mg or from 4 mg to 16 mg; and
(b) a 6-propylamino-4,5,6,7-tetrahydro-1,3-benzothiazole-2-amine selected from the group consisting of pramipexole and pharmaceutically acceptable salts and solvates thereof, in an amount equivalent to from 0.125 mg to 42 mg or, especially at the beginning of the treatment, from 1.5 mg to 20 mg or from more than 6 mg to 20 mg of pramipexole dihydrochloride monohydrate,
in admixture with a pharmaceutical carrier or vehicle.

More particularly, in said fixed-dose combination, said 6-propylamino-4,5,6,7-tetrahydro-1,3-benzothiazole-2-amine Component (b) is pramipexole dihydrochloride monohydrate in a dose-range per IR-unit form selected from the group consisting of from more than 4.5 mg to 21 mg, from more than 6 mg to 21 mg, and from 6.5 mg to 21 mg of pramipexole dihydrochloride monohydrate; or in a dose-range per ER-unit form selected from the group consisting of from more than 4.5 mg to 42 mg, from more than 6 mg to 42 mg, and from 6.5 mg to 42 mg.

The Pharmaceutical Compositions

For the intended use in the treatment of synucleinopathies in combination with 6-propylamino-4,5,6,7-tetrahydro-1,3-benzothiazole-2-amine, the 5HT3-antagonist is formulated in a pharmaceutical composition, wherein said 5HT3-antagonist is in admixture with a pharmaceutical carrier or vehicle.

In particular, as set forth above, according to the present invention the aforementioned 5HT3-antagonist and 6-propylamino-4,5,6,7-tetrahydro-1,3-benzothiazole-2-amine, separately or together, are normally formulated in a pharmaceutical composition useful as a medicament for the treatment of a patient suffering from a synucleinopathy.

The pharmaceutical compositions may be formulated in oral forms such as tablets or gelatin capsules wherein the 6-propylamino-4,5,6,7-tetrahydro-1,3-benzothiazole-2-amine or a pharmaceutically acceptable salt or solvate thereof or the 5HT3-antagonist or both the active ingredients are in admixture with a carrier or vehicle that may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of 6-propylamino-4,5,6,7-tetrahydro-1,3-benzothiazole-2-amine (or pharmaceutically acceptable salt or solvate thereof), or of 5HT3-antagonist, or of both the active ingredients. The oral formulations can also be in form of capsules allowing the extended release the 6-propylamino-4,5,6,7-tetrahydro-1,3-benzothiazole-2-amine (or pharmaceutically acceptable salt or solvate thereof), or of 5HT3-antagonist, or of both the active ingredients.

The pharmaceutical compositions may also be formulated in TTS, such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

"Transdermal drug delivery system" provides transdermal delivery using transdermal drug formulations and transdermal patches incorporating such transdermal drug formulations. For example, the transdermal drug delivery system may include a composition in form of a patch, a cream, a gel, a lotion or a paste comprising a 5HT3-antagonist (such as ondansetron). Examples of transdermal formulations may include, but are not limited, to those as described in U.S. Pat. No. 6,562,368, a transdermal gel formulation as described in U.S. Pat. Nos. 7,029,694; 7,179,483; 8,241,662 and US 2009/0018190, a transdermal or transmucosal pharmaceutical formulation, that can be utilized for topical or transdermal application, such that solutions, creams, lotions, sprays, ointment, gels, aerosols and patch drug deliveries as described in WO 2005/039531, US2007/022379, US 2010/0216880, US 2014/0037713 and U.S. Pat. No. 8,652,491, a transdermal absorption preparation as described in WO2013/061969 and US 2014/0271796, the disclosures of which are herein incorporated by reference in their entirety. The transdermal patches may also include, but are not limited to, a patch pump having an in-dwelling rigid catheter with flexible features and/or a flexible catheter attachment as described in U.S. Pat. No. 9,782,536, a selectively activatable patch pump as described in U.S. Pat. No. 9,724,462, a patch pump attached to a wireless communication system as described in U.S. Pat. No. 9,623,173, a conformable patch pump as described in U.S. Pat. No. 9,616,171, an infusion pump as described in U.S. Pat. No. 8,915,879, a portable infusion drug delivery as described in U.S. Pat. No. 8,480,649, a micropump as described in U.S. Pat. No. 8,282,366, and a patch pump as described in U.S. Pat. No. 7,828,771; the disclosures of which are herein incorporated by reference in their entirety. Other transdermal patches may include, but are not limited to, a patch in which oxybutynin is incorporated in an adhesive agent layer composition comprises the acrylic-based polymer as the adhesive base agent, and the acrylic-based polymer is a copolymer of polymethyl methacrylate with a polyacrylateas described in U.S. Pat. No. 8,802,134, a patch consisting of a support layer and of an adhesive agent layer arranged on the at least one surface of the support layer as described in U.S. Pat. No. 8,877,235, a patch using a monoglyceride or a mixture of monoglycerides of fatty acids as skin permeation-enhancer as described in U.S. Pat. Nos. 5,441,740 and 5,500,222, a patch for using a monoglyceride or a mixture of monoglycerides plus a lactate ester as skin permeation-enhancer as described in U.S. Pat. Nos. 5,686,097; 5,747,065; 5,750,137 and 5,900,250, a patch with a non-rate controlling tie layer on the skin-proximal surface of the reservoir, not affecting the drug release as described in U.S. Pat. Nos. 5,614,211 and 5,635,203, a patch using triacetin as permeation enhancer as described in U.S. Pat. Nos. 5,212,199, 5,227,169, 5,601,839 and 5,834,010, a patch with a matrix mass in the form of a layer which is self-adhesive, and in which the matrix mass consists of ammonium-group-containing (meth)acrylate copolymers as described in U.S. Pat. No. 6,555,129, a transdermal patch as described in U.S. Pat. Nos. 6,743,441; 7,081,249; 7,081,250; 7,081,251; 7,081,252 and 7,087,241; the disclosures of which are herein incorporated by reference in their entirety. Preferably, the transdermal drug delivery system is a patch, a patch pump, an infusion pump, or a micropump.

In the above pharmaceutical compositions, the preferred 5HT3-antagonist active ingredient is ondansetron base or its hydrochloride dihydrate, or dolasetron base or dolasetron mesylate monohydrate, and the preferred 6-propylamino-4,5,6,7-tetrahydro-1,3-benzothiazole-2-amine active ingredient is pramipexole base or pramipexole dihydrochloride monohydrate.

In the pharmaceutical compositions of the present invention for oral, subcutaneous, intravenous, transdermal or topical administration, the active ingredients are preferably administered in the form of dosage units, in admixture with the classic pharmaceutical carriers or vehicles.

The dosage, i.e. the amount of active ingredient in a single dose to be administered to the patient, can vary widely depending on the age, weight, and the health condition of the patient. This dosage includes the administration of a dose from 1 μg to 300 mg according to the potency of each 5HT3-antagonist and the age of the patient, and from 1.5 mg to 1500 mg of 6-propylamino-4,5,6,7-tetrahydro-1,3-benzothiazole-2-amine, according to the age of the patient, from one to three times a day by intravenous, subcutaneous, oral, or transcutaneous administration, and according to the strength of the doses of the each of the active ingredients.

If the 5HT3-antagonist is ondansetron hydrochloride dihydrate, said dosage ranges from 2 mg to 32 mg, from 4 mg to 32 mg, or from 4 mg to 16 mg (in ondansetron base); and, if the 6-propylamino-4,5,6,7-tetrahydro-1,3-benzothiazole-2-amine is pramipexole dihydrochloride monohydrate, said dosage ranges from 0.125 mg to 42 mg, preferably from 1.5 mg to 42 mg or, especially at the beginning of the treatment, from 1.5 mg to 20 mg.

A preferred composition advantageously will contain pramipexole or pharmaceutically acceptable salt thereof in an amount per unit form equivalent to from more than 4.5 mg 42 mg, advantageously from more than 6 mg to 42 mg or from 6.5 mg to 42 mg of pramipexole dihydrochloride monohydrate.

In the case of the initial treatment, said pramipexole or pharmaceutically acceptable salt or solvate thereof is in an amount equivalent to from more than 4.5 mg to 20 mg, from more than 6 mg to 20 mg, or from 6.5 mg to 20 mg of pramipexole dihydrochloride monohydrate.

All the above pramipexole dosage ranges per unit form also include low doses that can be used especially in the case of the initial titration of the pramipexole daily dose. However, according to the present invention, the therapeutically effective pramipexole or a pharmaceutically acceptable salt or solvates thereof dose-regimen in the treatment of the synucleinopathies with the above-illustrated combination, including fixed-dose combinations, is equivalent to more than 4.5 mg/day to 42 mg/day, preferably more than 6 mg/day to 42 mg/day, of pramipexole dihydrochloride monohydrate.

The combination of the present invention, by allowing the administration of pramipexole doses higher than the maximum recommended dose approved for the relief of motor symptom of Parkinson disease, will also allow the full expression of the pramipexole efficacy and represents a new tool for the treatment of a synucleinopathy such as Parkinson's disease, Lewy body disease (LBD) or dementia with Lewy bodies (DLB), parkinsonian disorders associated with glucocerebrosidase (GBA) mutations, Alzheimer's disease, the Lewy body variant of AD, neurodegeneration with brain iron accumulation and multiple system atrophy.

The pharmaceutical compositions of the present invention are formulated with the classic excipients suitable for different ways of administration. Particularly advantageous are the formulations in the form of tablets, multi-score tablets, coated tables, orally disintegrating tablets, extended release tablets, hard or soft capsules, extended-release capsules, patches for transdermal administration, liquid oral solutions, syrups or suspensions in a predetermined unit form, and vials for the intravenous or subcutaneous administration.

Thus, for example, a pharmaceutical composition according to the present invention to be administered in combination with 6-propylamino-4,5,6,7-tetrahydro-1,3-benzothiazole-2-amine (preferably pramipexole dihydrochloride monohydrate in an amount/IR-unit form of from 0.125 mg to 21 mg, preferably from 3 mg to 21 mg, or, in some cases, in an amount/IR-unit form of from 0.125 mg to 10 mg, normally from 1.5 mg to 10 mg, preferably from 1.6 to 10 mg, to be administered at a daily dose of from 0.375 mg to 42 mg, in some cases of from 3 mg to 20 mg, preferably from more than 6 mg to 20 mg, may comprise alosetron hydrochloride, in an amount/unit dose (in alosetron) of from 0.25 mg to 2 mg to be administered at a daily dose of from 0.25 mg to 3 mg; azasetron hydrochloride, in an amount/unit dose of from 5 mg to 10 mg to be administered at a daily dose of from 15 mg to 20 mg; dolasetron mesylate monohydrate, in an amount/unit dose (in dolasetron mesylate) of from 25 mg to 200 mg to be administered at a daily dose of from 75 mg to 200 mg; granisetron hydrochloride, in an amount/unit dose equivalent to from 0.5 mg to 2 mg granisetron base, to be administered at a daily dose of from 1.5 mg to 8 mg; ondansetron hydrochloride dihydrate, in an amount/unit dose equivalent to from 2 mg to 8 mg ondansetron base, to be administered at a daily dose of from 6 to 32 mg; palonosetron hydrochloride, in an amount/unit dose equivalent to from 0.25 mg to 0.5 mg palonosetron base, to be administered at a daily dose of from 0.75 to 2 mg; ramosetron hydrochloride, in an amount/unit dose of from 50 µg to 20 mg to be administered at a daily dose of from 75 mcg to 40 mg; and tropisetron hydrochloride, in an amount/unit dose equivalent to from 2.5 mg to 5 mg tropisetron base, to be administered at a daily dose of from 7.5 to 20 mg.

In the case of pediatric or obese patients, the 5HT3-antagonist daily dose may be decided on the basis of the body weight. Thus, for example, azasetron hydrochloride may be administered at a daily dose of 0.4-0.5 mg/kg, dolasetron mesylate may be administered at a daily dose of 9-9.5 mg/kg, granisetron hydrochloride may be administered at a daily dose of 0.09-0.11 mg/kg, ondansetron hydrochloride dihydrate may be administered at a daily dose of 0.45-0.55 mg/kg, palonosetron hydrochloride may be administered at a daily dose of 0.03 mg/kg and tropisetron hydrochloride may be administered at a daily dose of 0.5-0.6 mg/kg.

Example 1

The ability of the 5HT3-antagonists to prevent the gastrointestinal (GI) adverse effects (AEs) of pramipexole in humans was tested.

A Phase I study was conducted in subjects receiving a single oral dose of pramipexole dihydrochloride monohydrate ("pramipexole") with or without a single oral dose of ondansetron hydrochloride dihydrate ("ondansetron"). The study was single center, single-blind study.

The objective of the study was to demonstrate that ondansetron could safely attenuate the gastro-intestinal side effects of pramipexole given in doses equivalent or higher than those approved in the treatment of Parkinson's Disease or shown in clinical trials to be effective in the treatment of depression.

To be enrolled in the study, participants the following inclusion/exclusion key criteria:

Key Inclusion Criteria
1. Male and female subjects aged 20-45 years old both ages included.
2. Females of childbearing potential must agree to be abstinent or else use any two of the following medically acceptable forms of contraception from the Screening Period through 14 days after the study Exit Visit: condom with spermicidal jelly, diaphragm or cervical cap with spermicidal jelly, or intrauterine device (IUD). A female whose male partner has had a vasectomy must agree to use one additional form of medically acceptable contraception. Subjects must agree to practice the above birth control methods for 14 days after the final visit as a safety precaution.
3. Females of non-childbearing potential, defined as surgically sterile (status post-hysterectomy, bilateral oophorectomy, or bilateral tubal ligation) or post-menopausal for at least 12 months, do not require contraception during the study. The reason must be documented in the source documents.
4. Males with female partners of childbearing potential must agree to use a highly effective, medically acceptable form of contraception from the Screening Period through 14 days after the study Exit Visit. Males with female partners of childbearing potential who themselves are surgically sterile (status post vasectomy) must agree to use condoms with spermicide over the same period of time. Male subjects must agree to practice the above birth control methods for 14 days after the final visit as a safety precaution.
5. Subjects must be in good health as determined by their medical history including personal and family psychiatric history and results of physical examination, electrocardiogram (ECG), vital signs, and laboratory tests. A subject with a medical abnormality may be included only if the investigator or designee considers that the abnormality will not introduce significant additional risk to the subject's health or interfere with study objectives. 6. Subjects must be able to clearly and reliably communicate changes in their medical condition.
7. Subjects with a body mass index (BMI) between 19.0 and 32.0 kg/m$^2$ (both inclusive).
8. Subjects able to swallow multiple pills or capsules simultaneously.
9. Subjects must have signed an informed consent form indicating that they understand the purpose of and procedures required for the study and are willing to participate in the study and comply with the study procedures and restrictions.

Key Exclusion Criteria:
The criteria for exclusion of a subject from enrollment in the study were as follows:
1. Any clinically relevant acute or chronic diseases which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study drugs.
3. History of substance abuse, known drug addiction, or positive test for drugs of abuse or alcohol.
4. History of drug or other significant allergy.
5. Known hypersensitivity to pramipexole, or to ondansetron or similar serotonin receptor antagonists, or to aprepitant or similar Substance P/NK1 receptor antagonists.
5. History of and/or current QT interval prolongation, congenital long QT syndrome, electrolyte abnormalities (e.g., hypokalemia or hypomagnesemia), congestive heart failure, bradyarrhythmias or other medicinal products that lead to QT prolongation or 1st degree AV block at Screening, Day −1, or pre-dose, ≥450 QTcF for males and ≥470 QTcF for females.
7. Treatment with centrally active drugs or antiemetics, within 1 months of study entry.

8. Tobacco or nicotine users (except subjects who stopped using tobacco or nicotine 1 year or more before enrollment in the study).
9. Excessive daily consumption of xanthines containing drinks (i.e. >500 mg/day of caffeine).
10. Subjects unwilling to curtail prolonged intensive physical exercise during the study conduct (from the Screening visit until the last dose of study drug).
11. Positive test result for hepatitis B surface antigen, hepatitis C antibody.
12. Positive test result for HIV 1 or 2 serology.
13. Likely to need any medical or dental treatment during the study period.
14. Use of any prescription or over-the-counter medication within 14 days prior to admission on Day-1. In addition any medications with central effects are prohibited for a period equal to 5 times the drug half-life prior to admission (Day −1), should this period be longer than 14 days.
15. Subjects unlikely to co-operate during the study, and/or be questionably compliant in the opinion of the investigator.
16. Subjects unable to be contacted in case of an emergency.
17. Intake of an investigational drug within 30 days of study entry.
18. Show evidence of suicidal ideation within the last 6 months as assessed by the C-SSRS (Columbia Suicide Severity Rating Scale) at Screening.

Following enrollment in the study, participants received single increasing oral doses of pramipexole given once daily in the morning (Period 1 of the study). The starting dose of pramipexole was 0.5 mg and the dose was increased daily by 0.5 mg increments. Once a subject had reached his/her first intolerable dose (FID-1), upward dose escalation was discontinued. First intolerable dose (FID) was defined as:
one (1) episode of vomiting; or
Two (2) episodes of retching, or
One (1) episode of severe nausea (Grade 3; defined as nausea interfering with activities of daily living or inadequate oral caloric or fluid intake; tube feeding, total parenteral nutrition or hospitalization indicated) lasting more than 1 hour, or
Three (3) consecutive episodes at every 4 hour ratings of moderate nausea (Grade 2; defined as subjectively symptomatic, but not interfering with activities of daily living), or
One (1) episode of moderate diarrhea (Grade 2; defined as 4-6 stools more than at baseline).

When a subject reached FID-1 on pramipexole alone, the subject was washed out for at least 5 days, and then entered Period 2 of the study during which the subject received single daily oral doses of pramipexole starting at 0.5 mg and titrated upward by 0.5 mg increments, together with oral ondansetron hydrochloride dihydrate (10 mg, equivalent to 8 mg ondansetron base) until subjects again reached an intolerable dose defined as above. The FID on oral pramipexole plus oral ondansetron was referred to as FID-2.

If a subject reached FID-2 during Period 2 at the same or lower dose than FID-1, and providing the investigator judged there were no safety issues and the subject was consenting, the subject received the same dose of pramipexole as the FID-2 dose together with a higher dose of oral ondansetron hydrochloride dihydrate (20 mg, equivalent to 16 mg ondansetron base) on the next day and the protocol specified that said subject should continue with the remainder of the dose titration with the higher dose of oral ondansetron hydrochloride dihydrate (20 mg, equivalent to 16 mg ondansetron base) until they reach the intolerable dose (FID2+). All other provisions of the protocol remained unchanged. Assessments were the same as those planned for the dose escalation day.

On each study day, subjects were followed up for up to 8 hours following drug administration for AEs, vital signs, ECGs. In addition, a laboratory panel was taken at screening and at the end of the study.

Three subjects were enrolled in the study. The following Table 1 summarizes the demographic characteristics of the subjects.

TABLE 1

Demographic Characteristics of Subjects Enrolled in the Study

| Subject ID | Gender | Age (years) | Baseline Weight (kg) |
|---|---|---|---|
| 1001 (019) | Female | 40 | 76.4 kg |
| 1005 (027) | Female | 30 | 54.8 kg |
| 1006 (001) | Male | 41 | 99.1 kg |
| 1007 (004) | Male | 38 | 64.9 kg |
| 1008 (008) | Male | 39 | 81.8 kg |

All subjects reached FID-1 (pramipexole alone) during the study. The dose limiting toxicity was gastro-intestinal adverse events in all 5 subjects. For all subjects FID-2 was higher than FID-1. During Period 2 of the study, 3 of the 5 subjects tolerated the maximum pramipexole dose allowed by the protocol of 6 mg and therefore these subjects did not reach FID-2 (pramipexole with ondansetron). In other words, concomitant administration of ondansetron with pramipexole prevented the occurrence of dose-limiting gastro-intestinal adverse events associated with high doses of pramipexole. Table 2 lists for each subject the values for FID-1 (on pramipexole alone) and FID-2 (on pramipexole+ondansetron).

TABLE 2

Listing of First Intolerable Doses (FID) values

| Subject ID | FID-1 (Pramipexole alone) | FID-1 Dose Limiting Adverse Event | FID-2 Pramipexole + Ondansetron |
|---|---|---|---|
| 1001 | 2.5 mg | GI issues | >6.0 mg |
| 1005 | 2.0 mg | Retching | 3.0 mg |
| 1006 | 0.5 mg | Moderate nausea | 1.0 mg |
| 1007 | 4.5 mg | Severe nausea | >6.0 mg |
| 1008 | 1.5 mg | Vomiting | >6.0 mg |

As shown in the following Table 3, the Maximum Tolerated Dose (MTD) during Period 2 was higher than MTD during Period 1 in all subjects, and in 2 subjects MTD-2 was increased by more than 3-fold.

TABLE 3

Listing of Maximum Tolerated Doses (MTD)

| Subject ID | MTD-1 (Pramipexole alone) | Maximal Tolerated Dose Pramipexole + Ondansetron | MTD2/MTD1 |
|---|---|---|---|
| 1001 | 2.0 mg | >6.0 mg | >3.0 |
| 1005 | 1.5 mg | 2.5 mg | 1.67 |
| 1006 | NA (not tolerated at 0.5 mg) | 0.5 mg | >1.0 |
| 1007 | 4.0 mg | >6.0 mg | >1.5 |
| 1008 | 1.0 mg | >6.0 mg | >6 |

MTD: Maximum Tolerated Dose

Taken together, results showed that the co-administration of ondansetron with pramipexole attenuated dose-limiting gastro-intestinal adverse effects reported with pramipexole alone, thus showing that a 5HT3-antagonist enables the administration to a human being of pramipexole in doses otherwise non-tolerated when administering pramipexole alone.

In conclusion, the co-administration of ondansetron with pramipexole inhibited the occurrence of gastro-intestinal AEs associated with pramipexole given alone, thus enabling doses of pramipexole to be safely and tolerably raised by more than 2-fold, thereby allowing a far greater efficacy of this drug.

REFERENCES

Al-Mansoori et al. 2013: Al-Mansoori K M, Hasan M Y, Al-Hayani A, El-Agnaf M, "*The role of α-synuclein in neurodegenerative diseases: from molecular pathways in disease to therapeutic approaches*"; Curr. Alzheimer Res. 2013 July; 10(6): 559-568.

Chen et al. 2016: Chen M, Weiwei Yang W, Li Xin, X, Li Xuran, Wang P, Feng Yue F, Yang H, Chan P, and Yu S; "*Age-and brain region-dependent α-synuclein oligomerization is attributed to alterations in intrinsic enzymes regulating α-synuclein phosphorylation in aging monkey brains*"; Oncotarget. 2016 Feb. 23; 7(8): 8466-8480.

Cho J-R et al 2016: Cho J-R, Duong A V, Nguyen L T T, Chi S-C. "*Design of transdermal matrix patch containing ondansetron*". J Pharm Investigation. 2016 46(7): 677-684.

Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000; 11(2):58-65.

Inden et al. 2009: Inden M, Kitamura Y, Tamaki A, Yanagida T, Shibaike T, Yamamoto A, Takata K, Yasui H, Taira T, Ariga H, Taniguchi T; "*Neuroprotective effect of the antiparkinsonian drug pramipexole against nigrostriatal dopaminergic degeneration in rotenone-treated mice.*"; Neurochem Int. 2009 December; 55(8):760-7.

Jellinger K A 2008a: Jellinger K A, "*A critical reappraisal of current staging of Lewy-related pathology in human brain*"; Acta Neuropathol. 2008 July; 116(1): 1-16.

Jellinger K A 2008b: Jellinger K A, "*Neuropathological aspects of Alzheimer disease, Parkinson disease and frontotemporal dementia*"; Neurodegener. Dis. 2008; 5(3-4): 118-121.

Kakimura et al. 2001: Kakimura J, Kitamura Y, Takata K, Kohno Y, Nomura Y, Taniguchi T; "*Release and aggregation of cytochrome c and alpha-synuclein are inhibited by the antiparkinsonian drugs, talipexole and pramipexole*"; Eur J Pharmacol. 2001 Apr. 6; 417(1-2):59-67.

Kim et al. 2004: Kim S, Seo J H, Suh Y H, "*Alpha-synuclein, Parkinson's disease, andAlzheimer's disease*"; Parkinsonism Relat. Disord. 2004 May; 10 Suppl. 1: S9-13.

Koland M et al. 2010: Koland M, Sandeep V P. Charyulu N R. "*Ondansetron Hydrochloride: Effect of Additives on in vitro Drug Release and Mucosal Permeation*". J Young Pharmacists. 2010, 2(3):216-222.

Luo et al. 2016: Luo H T, Zhang J P, Miao F; "*Effects of pramipexole treatment on the α-synuclein content in serum exosomes of Parkinson's disease patients*"; Exp Ther Med. 2016 September; 12(3):1373-1376).

Marques and Outeiro 2012: Marques O, Outeiro T F; "*Alpha-synuclein: from secretion to dysfunction and death*"; Cell Death Dis. 2012 Jul. 19; 3:e350. doi: 10.1038/cddis.2012.94.

Ono et al. 2013: Ono K, Takasaki J, Takahashi R, Ikeda T, Yamada M; "*Effects of antiparkinsonian agents on β-amyloid and α-synuclein oligomer formation in vitro*"; J Neurosci Res; 2013 October; 91(10):1371-81).

O'Regan et al 2017: O'Regan G, DeSouza R M, Balestrino R, "*Glucocerebrosidase Mutations in Parkinson Disease*" J Parkinson's Dis 7 (2017) 411-422—DOI 10.3233/JPD-171092.

Prusiner S B et al. 2015: Prusiner S B, Woerman A L, Mordes D A, Watts J C, Rampersaud R, Berry D B, Patel S, Oehler A, Lowe J K, Kravitz S N, Geschwind D H, Glidden D V, Halliday G M, Middleton L T, Gentleman S M, Grinberg L T, Giles K, "*Evidence for α-synuclein prions causing multiple system atrophy in humans with parkinsonism*"; Proc Natl Acad Sci USA; 2015, Sep. 22; 112(38):E5308-17.

Schapira et al. 2013: Schapira A H, McDermott M P, Barone P, Comella C L, Albrecht S, Hsu H H, Massey D H, Mizuno Y, Poewe W, Rascol O, Marek K. "Pramipexole in patients with early Parkinson's disease (PROUD): a randomised delayed-start trial"; Lancet Neurol. 2013 August; 12(8):747-55).

Schneider C S and Mierau J, 1987: Schneider C S, Mierau J "*Dopamine autoreceptor agonists: resolution and pharmacological activity of 2,6-diaminotetrahydrobenzothiazole and an aminothiazole analogue of apomorphine*"; J. Med Chem. 1987 March; 30(3):494-8.

Shi et al. 2014: Shi M, Liu C, Cook T J, Bullock K M, Zhao Y, Ginghina C, Li Y, Aro P, Dator R, He C, Hipp M J, Zabetian C P, Peskind E R, Hu S C, Quinn J F, Galasko D R, Banks W A, Zhang J; "*Plasma exosomal α-synuclein is likely CNS-derived and increased in Parkinson's disease*"; Acta Neuropathol. 2014 November; 128(5):639-50. doi: 10.1007/s00401-014-1314-y. Epub 2014 Jul. 6.

Soria et al 2017: Soria F N, Engeln M, Martinez-Vicente M, Glangetas C, Lopez-Gonzales J, Dovero S, Dehay B, Normand E, Vila M, Lopez-Gonzales M J, Favereaux A, Georges F, Lo Bianco C, Bezard E, Fernagut; "*Glucocerebrosidase deficiency in dopaminergic neurons induces microglial activation without neurodegeneration*"; Hum Mol Genet 2017 July; 26(14):2603-2615.

Stuendl A, Kunadt M, Kruse N, Bartels C, Moebius W, Danzer K M, Mollenhauer B, Schneider A; "*Induction of alpha-synuclein in aggregate formation by CSF exosomes from patients with Parkinson's disease and dementia with Lewy bodies*" Brain 2016, 139; 481-494.

The invention claimed is:

1. A pharmaceutical composition in dosage unit form which comprises
   (a) a 5HT3-antagonist, in an amount per unit form of from 1 μg to 300 mg; and
   (b) a 6-propylamino-4,5,6,7-tetrahydro-1,3-benzothiazole-2-amine selected from the group consisting of the racemate or a pharmaceutically acceptable salt thereof, in an amount per unit form equivalent to from 0.75 mg to 90 mg of pramipexole dihydrochloride monohydrate; pramipexole or a pharmaceutically acceptable salt thereof, in an amount per unit form equivalent to from 0.375 mg to 45 mg of pramipexole dihydrochloride monohydrate; and an (R)/(S)-mixture, in an amount per unit form of from 50 mg to 3000 mg, inclusive of an (S)-enantiomer or a pharmaceutically acceptable salt thereof in amount per unit form equivalent to from 0.375 mg to 45 mg of pramipexole dihydrochloride monohydrate, in admixture with a pharmaceutical carrier or vehicle.

2. The composition of claim 1, wherein said 6-propylamino-4,5,6,7-tetrahydro-1,3-benzothiazole-2-amine is pramipexole or a pharmaceutically acceptable salt thereof, in an amount per unit form equivalent to from more than 4.5 mg to 42 mg of pramipexole dihydrochloride monohydrate.

3. The composition of claim 1, wherein said 6-propylamino-4,5,6,7-tetrahydro-1,3-benzothiazole-2-amine is pramipexole or a pharmaceutically acceptable salt thereof, in an amount per unit form equivalent to from more than 6 mg to 42 mg of pramipexole dihydrochloride monohydrate.

4. The composition of claim 1, wherein said 6-propylamino-4,5,6,7-tetrahydro-1,3-benzothiazole-2-amine is pramipexole or a pharmaceutically acceptable salt thereof, in an amount per unit form equivalent to from 6.5 mg to 42 mg of pramipexole dihydrochloride monohydrate.

5. The composition of claim 1, wherein said 5HT3-antagonist is ondansetron hydrochloride dihydrate, in an amount per unit for equivalent to from 2 mg to 32 mg of ondansetron base, and said 6-propylamino-4,5,6,7-tetrahydro-1,3-benzothiazole-2-amine is pramipexole or a pharmaceutically acceptable salt thereof, in an amount per unit form equivalent to from 0.375 mg to 42 mg of pramipexole dihydrochloride monohydrate.

6. The composition of claim 1, wherein said 6-propylamino-4,5,6,7-tetrahydro-1,3-benzothiazole-2-amine is pramipexole or a pharmaceutically acceptable salt thereof, in an amount per IR-unit form equivalent to from more than 6 mg to 22.5 mg of pramipexole dihydrochloride monohydrate.

7. The composition of claim 1, wherein said 6-propylamino-4,5,6,7-tetrahydro-1,3-benzothiazole-2-amine is pramipexole or a pharmaceutically acceptable salt thereof, in an amount per ER-unit form equivalent to from more than 6 mg to 45 mg of pramipexole dihydrochloride monohydrate.

8. The composition of claim 1, wherein said 5HT3-antagonist is selected from the group consisting of alosetron and pharmaceutically acceptable salts and solvates thereof, azasetron and pharmaceutically acceptable salts and solvates thereof, bemesetron and pharmaceutically acceptable salts and solvates thereof, cilansetron and pharmaceutically acceptable salts and solvates thereof, dolasetron and pharmaceutically acceptable salts and solvates thereof, fabesetron and pharmaceutically acceptable salts and solvates thereof, granisetron and pharmaceutically acceptable salts and solvates thereof, itasetron and pharmaceutically acceptable salts and solvates thereof, lerisetron and pharmaceutically acceptable salts and solvates thereof, lurosetron and pharmaceutically acceptable salts and solvates thereof, ondansetron and pharmaceutically acceptable salts and solvates thereof, palonosetron and pharmaceutically acceptable salts and solvates thereof, ramosetron and pharmaceutically acceptable salts and solvates thereof, ricasetron and pharmaceutically acceptable salts and solvates thereof, tropisetron and pharmaceutically acceptable salts and solvates thereof, and zatosetron and pharmaceutically acceptable salts and solvates thereof.

9. The composition of claim 5, wherein said 6-propylamino-4,5,6,7-tetrahydro-1,3-benzothiazole-2-amine is pramipexole or a pharmaceutically acceptable salt thereof, in an amount per unit form equivalent to from more than 4.5 mg to 42 mg of pramipexole dihydrochloride monohydrate.

10. The composition of claim 5, wherein said 6-propylamino-4,5,6,7-tetrahydro-1,3-benzothiazole-2-amine is pramipexole or a pharmaceutically acceptable salt thereof, in an amount per unit form equivalent to from more than 6.0 mg to 42 mg of pramipexole dihydrochloride monohydrate.

11. The composition of claim 5, wherein said 6-propylamino-4,5,6,7-tetrahydro-1,3-benzothiazole-2-amine is pramipexole or a pharmaceutically acceptable salt thereof, in an amount per unit form equivalent to from 6.5 mg to 42 mg of pramipexole dihydrochloride monohydrate.

* * * * *